Figure 1:
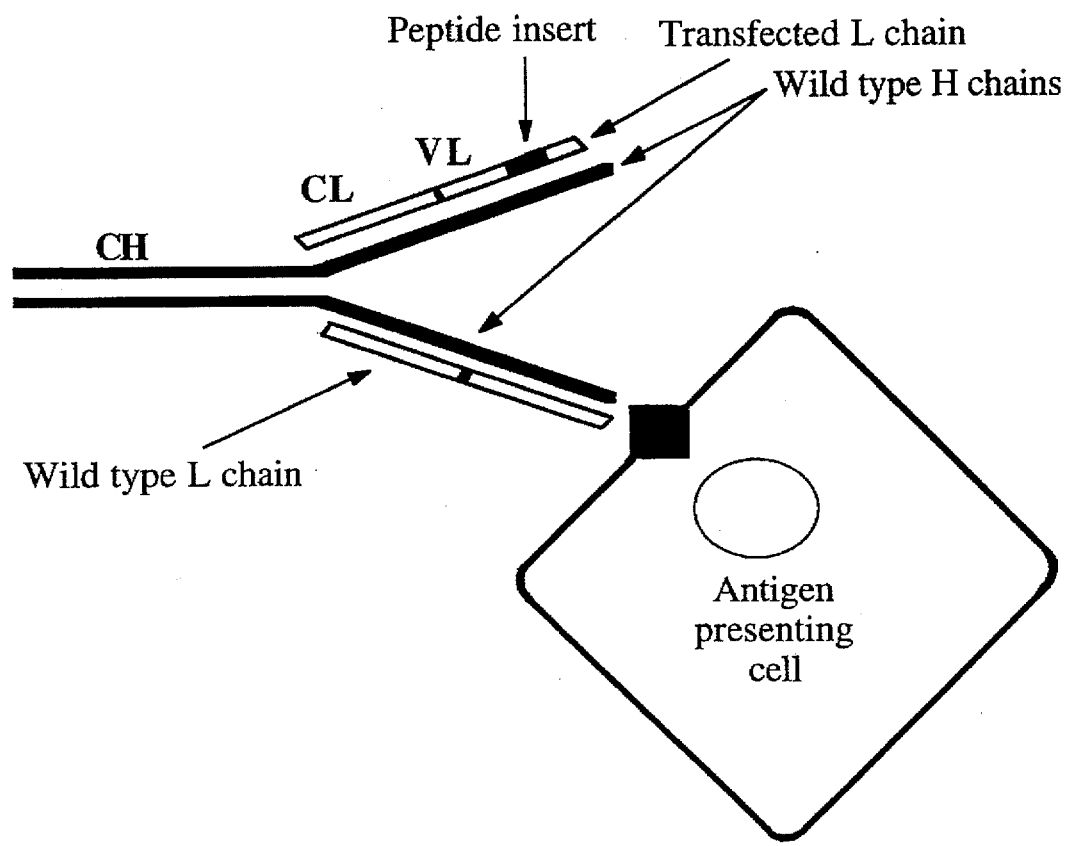

United States Patent [19]

Nemazee

[11] Patent Number: 5,698,679

[45] Date of Patent: Dec. 16, 1997

[54] PRODUCT AND PROCESS FOR TARGETING AN IMMUNE RESPONSE

[75] Inventor: David A. Nemazee, Denver, Colo.

[73] Assignee: National Jewish Center for Immunology and Respiratory Medicine, Denver, Colo.

[21] Appl. No.: 309,006

[22] Filed: Sep. 19, 1994

[51] Int. Cl.$^6$ .................. C12P 21/08; A61K 39/395; A61K 39/40; A61K 39/42

[52] U.S. Cl. .................. 530/387.3; 424/130.1; 424/133.1; 424/134.1

[58] Field of Search ............... 530/387.3; 424/130.1

[56] References Cited

PUBLICATIONS

Favalong Immunology and All Biology 1993 71 571–581.
Culpepy et al. Moleclar Biochem Parast p. 1992 54 (1) pp. 51–62.
Chuo et al. J. Allergy Clin. Immunol. 1992 89 pp. 95–102.
Greene et al. Mol. Immunol. 1992 29(2) pp. 257–262.
Brumeanu et al., "Efficient Loading of Identical Viral Peptide Onto Class II Molecules by Antigenized Immunoglobulin and Influenza Virus", pp. 1795–1799, 1993, *J. Exp. Med.*, vol. 178.
Carayannioris et al., "Adjuvant–Free IgG Responses Induced with Antigen Coupled to Antibodies Against Class II MHC", pp. 59–61, 1987, *Nature*, vol. 327.
Gosselin et al., "Enhanced Antigen Presentation Using Human FCγ Receptor (Monocyte/Macrophage)–Specific Immunogens", pp. 3477–3481, 1992, *J. Immunol.*, vol. 149, No. 11.
Ozaki et al., "Antibody Conjugates Mimic Specific B Cell Presentation of Antigen: Relationship Between T and B Cell Specificity", pp. 4133–4142, 1987, *J. Immunol.*, vol. 138, No. 12.

Skea et al., "Studies of the Adjuvant–Independent Antibody Response to Immunotargeting; Target Structure Dependence, Isotype Distribution, and Induction of Long Term Memory", pp. 3557–3568, 1993, *J. Immunol.*, vol. 151, No. 7.
Snider et al., "Enhanced Antigen Immunogenicity Induced by Bispecific Antibodies", pp. 1957–1963, 1990, *J. Exp. Med.*, vol. 171.
Snider et al., "Targeted Antigen Presentation Using Crosslinked Antibody Heteroaggregates", pp. 1609–1616, 1987, *J. Immunol.*, vol. 139, No. 5.
Watson et al., "New Generation Vaccines: Does Antibody Play a Directional Role in Antigen–Processing?", pp. 28–33, 1991, *Am. J. Trop. Med. Hyp.*, vol. 44(4) Suppl.
Zaghouani et al., "Presentation of a Viral T Cell Epitope Expressed in the CDR3 Region of a Self Immunoglobulin Molecule", pp. 224–227, 1993, *Science*, vol. 259.

*Primary Examiner*—Lila Feisee
*Assistant Examiner*—Yvonne Eyler
*Attorney, Agent, or Firm*—Sheridan Ross P.C.

[57] ABSTRACT

The present invention relates to a product and process for regulating an immune system using an immunoglobulin fusion protein capable of targeting a specific peptide precursor to a specific antigen presenting cell. Disclosed is a peptide precursor associated with an immunoglobulin molecule capable of binding to an antigen on the surface of an antigen presenting cell. Also disclosed is a nucleic acid molecule having a sequence encoding an immunoglobulin fusion protein comprising a peptide precursor and an immunoglobulin molecule. The invention is additionally directed to therapeutic reagents which can act as toleragens or immunogens useful in the regulation of an immune response.

27 Claims, 5 Drawing Sheets

PRODUCT AND PROCESS FOR TARGETING AN IMMUNE RESPONSE

FIELD OF THE INVENTION

The present invention relates to a product and process for the treatment of subjects in need of the abrogation or enhancement of immunological reactivities. More particularly, the present invention relates to an immunoglobulin fusion protein (hereinafter defined) and the use of such immunoglobulin fusion protein as immunoregulators to effect therapeutic objectives.

BACKGROUND OF THE INVENTION

A wide variety of medical treatments require regulation of the immune response in a patient. Such treatments include, for example, vaccinations, treatments for autoimmune diseases, immunodeficiency diseases, immunoproliferative diseases, and treatments involving the transplantation of organs and skin. Traditional reagents and methods used to regulate a subject's immune response often results in unwanted side effects. For example, immunosuppressive reagents such as cyclosporin A, azathioprine, and prednisone are used to suppress the immune system of a patient with an autoimmune disease or patients receiving transplants. Such reagents, however, suppress a patient's entire immune response, thereby crippling the ability of the patient to mount an immune response against infectious agents not involved in the original disease. Due to such harmful side effects and the medical importance of immune regulation, reagents and methods to regulate specific parts of the immune system have been the subject of study for many years.

Introduction of an antigen into a host initiates a series of events culminating in an immune response. In addition, self-antigens can result in immunological tolerance or activation of an immune response against self-antigens. A major portion of the immune response is regulated by presentation of antigen by major histocompatibility complex molecules (MHC molecules). MHC molecules bind to peptide fragments derived from antigens to form complexes that are recognized by T cell receptors on the surface of T cells, giving rise to the phenomenon of MHC-restricted T cell recognition. The ability of a host to react to a given antigen (responsiveness) is influenced by the spectrum of MHC molecules expressed by the host. Responsiveness correlates to the ability of specific peptide fragments to bind to particular MHC molecules.

T cell receptors (TCRs) recognize antigens that are bound by MHC molecules. Recognition of MHC complexed with peptide (MHC-peptide complex) by TCR can effect the activity of the T cell bearing the TCR. Thus, MHC-peptide complexes are important in the regulation of T cell activity and thus, in regulating an immune response.

There are two types of MHC molecules, class I and class II. MHC class I molecules are expressed on the surface of all cells and MHC class II are expressed on the surface of antigen presenting cells. MHC class II molecules bind to peptides derived from proteins made outside of an antigen presenting cell. In contrast, MHC class I molecules bind to peptides derived from proteins made inside a cell. In order to present peptide in the context of a class II molecule, an antigen presenting cell phagocytoses an antigen into an intracellular vesicle, in which the antigen is cleaved, bound to an MHC class II molecule, and then returned to the surface of the antigen presenting cell.

Prior to the present invention, immunoregulatory reagents used to treat immune disorders have suffered from a variety of problems. For example, immunoregulatory reagents used to immunosupress subjects, such as graft recipients and allergic individuals, are non-specific (i.e., regulate the function of many immune cell types) and therefore suppress a subject's entire immune system creating a substantial risk of infections. Immunoregulatory reagents which immunostimulate subjects, such as vaccines comprising antigens, are inefficient for a variety of reasons, including the fact that antigens are not directly recognized but need to be presented by antigen presenting cells. Thus, often substantial amounts of vaccine are required to obtain an effect. In addition, a vaccine often requires ancillary treatment with harmful reagents, such as adjuvants, to enhance the efficiency of the vaccine.

The present invention overcomes traditional problems with immunoregulatory reagents by targeting specific antigens to specific antigen presenting cells in vivo. In particular, the present invention overcomes the problem of variable outcomes which result from injecting antigens, to immunize or desensitize subjects, without specifically targeting antigen presenting cells. Specific targeting to a correct antigen presenting cell type can allow for a reduction in antigen dose, a more consistent response and consistent avoidance of unwanted side effects. In addition, the present invention enables a reduction or elimination of common additives to antigen preparations that promote immunization (e.g., adjuvants) which can cause damaging side effects.

Particular immunoglobulin:antigen complexes have been suggested by various investigators. Gosselin et al., pp. 3477-3481, 1992, *J. Immunol.*, Vol. 149; Ozaki et al., pp. 4133-4142, 1987, *J. Immunol.*, Vol. 138; Snider et al., pp. 1609-1616, 1987, *J. Immunol.*, Vol. 139; Snider et al., pp. 1957-1963, 1990, *J. Exp. Med.*, Vol. 171; Skea et al., pp. 3557-3568, 1993, *J. Immunol.*, Vol. 151; Carayanniotis et al., pp. 59-61, 1987, *Nature*, Vol. 327; and Watson et al., pp. 28-33, 1991, *Ann. J. Trop. Med. Hyg.*, Vol. 44; have disclosed chemically-conjugated immunoglobulin:antigen or peptide complexes. Production of immunoglobulin:antigen or peptide complexes by chemical conjugation is laborious. In addition, the quality of chemically-conjugated complexes is unpredictable because of the variability of the efficiency of conjugation and the heterogeneity of the synthetically derived antigens or peptides being conjugated. Zaghouani et al., pp. 224-227, 1993, *Science*, Vol. 259; and Brumeanu et al., pp. 1795-1799, 1993, *J. Exp. Med.*, Vol. 178; have disclosed recombinantly produced immunoglobulin:peptide complexes but do not teach the advantage of targeting such complexes to specific antigen presenting cells.

As such, there is a need for a product and process that allows for the cost-effective production of large quantities immunoglobulin fusion proteins capable of specifically targeting specific antigen presenting cells, the activity of which is predictable and reproducible.

SUMMARY

The present invention relates to a novel product and process for treatment of subjects in need of the abrogation or enhancement of immunological reactivities. The present invention includes a novel immunoglobulin fusion protein comprising a peptide precursor and an immunoglobulin molecule capable of binding to an antigen on the surface of an antigen presenting cell. The invention is particularly advantageous in that it provides a method for targeting a specific peptide precursor to a specific antigen presenting cell. Also included is a method to a produce immunoglobulin fusion protein of the present invention.

One embodiment of the present invention includes an immunoglobulin fusion protein comprising an immunoglobulin molecule linked to a peptide precursor, wherein the immunoglobulin molecule comprises a variable region capable of binding to an antigen on the surface of an antigen presenting cell. In a preferred embodiment, the peptide precursor is substituted for the CDR1 domain of the light chain V region of the immunoglobulin molecule.

Another embodiment of the present invention includes an immunoglobulin fusion protein comprising an immunoglobulin molecule associated with a peptide precursor, wherein said immunoglobulin molecule is capable of binding to an antigen that distinguishes between types of antigen presenting cells. In a preferred embodiment, the peptide precursor is linked to the immunoglobulin molecule.

A further embodiment of the present invention relates to a nucleic acid molecule having a sequence encoding an immunoglobulin light chain linked to a peptide precursor, wherein the immunoglobulin light chain is capable binding to a molecule on the surface of an antigen presenting cell when associated with a compatible immunoglobulin heavy chain. In a preferred embodiment, a nucleic acid molecule encodes a protein comprising both a $V_L$ and a $V_C$ region.

The present invention further relates to a recombinant cell having a recombinant molecule comprising a nucleic acid molecule operatively linked to an expression vector, the nucleic acid molecule having a sequence encoding at least a portion of an immunoglobulin fusion protein comprising an immunoglobulin molecule linked to a peptide precursor, wherein the immunoglobulin molecule comprises a variable region capable of binding to an antigen on the surface of an antigen presenting cell. Alternatively, the immunoglobulin fusion protein encoded by the recombinant molecule is capable of binding to an antigen that distinguishes between types of antigen presenting cells.

The immunoglobulin fusion proteins of the present invention can be used as a therapeutic reagent to treat subjects having immunological disorders. In one embodiment, the therapeutic reagent comprises a toleragen capable inducing immunological unresponsiveness to an antigen in a subject or an immunogen capable of inducing an immune response. In a preferred embodiment, a toleragen of the present invention comprises a monovalent immunoglobulin fusion protein. In an alternative preferred embodiment, an immunogen of the present invention comprises a multivalent immunoglobulin fusion protein. Also included is a method to regulate an immune response by administering to an animal an effective amount of an immunoglobulin fusion protein of the present invention.

BRIEF DESCRIPTION OF THE FIGURES

FIG. 1 illustrates the interaction of an immunoglobulin molecule with an APC.

FIG. 2 illustrates the recombinant molecule encoding the 3.83 light chain.

FIG. 3 illustrates the $OVA_{326-337}$ chimeric light chain.

FIG. 4 illustrates the expression of $OVA_{326-337}$ chimeric light chain by SP2/0 transfectomas.

FIG. 5 illustrates that the $OVA_{326-337}$ chimeric light chain is processed and presented by APCs to T cells.

DETAILED DESCRIPTION OF THE INVENTION

The present invention relates to a novel product and process for treatment of subjects in need of the abrogation or enhancement of immunological reactivities. The present invention includes a novel immunoglobulin fusion protein having at least two components: (1) a peptide precursor; and (2) an immunoglobulin molecule (as defined below) having a variable region capable of binding to an antigen on the surface of an antigen presenting cell. The invention is particularly advantageous in that it provides an peptide precursor associated with an immunoglobulin molecule capable of targeting an antigen presenting cell. The peptide precursor can be linked to the immunoglobulin molecule and specific antigen presenting cells can be targeted. In addition, the invention is particularly advantageous in that it provides for a method to develop immunosuppressive or immunostimulatory reagents having specific antigenic proteins by modifying the valency and/or antigen presenting cell binding specificity of an immunoglobulin fusion protein. A particular embodiment of an immunoglobulin fusion protein that is capable of targeting (i.e., delivering) an antigenic protein to an antigen presenting cell includes an antigenic protein associated with a variable region of an immunoglobulin fusion protein as described in detail below.

A naturally-occurring immunoglobulin molecule is a plasma protein comprising immunoglobulin domains. An immunoglobulin molecule comprises two types of chains. One type of chain is referred to as the heavy or H chain and the other is referred to as the light or L chain. The two chains are present in an equimolar ratio, and each immunoglobulin molecule has at least two H chains and at least two L chains. The two H chains are linked together by disulfide bonds and each H chain is linked to a L chain by a disulfide bond. There are only two types of L chains referred to as lambda (λ) and kappa (κ) chains. In contrast, there are five major H chain classes referred to as isotypes. The five classes include immunoglobulin M (IgM or μ), immunoglobulin D (IgD or δ), immunoglobulin G (IgG or λ), immunoglobulin A (IgA or α), and immunoglobulin E (IgE or ε). The distinctive characteristics between such isotypes are defined by the constant domain of the immunoglobulin and are discussed in detail below. Human immunoglobulin molecules comprise nine isotypes, IgM, IgD, IgE, four subclasses of IgG including IgG1 (γ1), IgG2 (γ72), IgG3 (γ3) and IgG4 (γ4), and two subclasses of IgA including IgA1 (α1) and IgA2 (α2).

Each H or L chain of an immunoglobulin molecule comprises two domains referred to as L chain variable regions ($V_L$ regions) and L chain C regions ($C_L$), and H chain V regions ($V_H$ regions) and H chain C regions ($C_L$ regions). A complete $C_H$ region comprises a CH1, CH2, CH3 domain and a hinge region. Together, one H chain and one L chain form an arm of an immunoglobulin molecule having an immunoglobulin V region. A complete immunoglobulin molecule comprises two arms, disulfide bonded by the H chain C regions of each arm. Thus, each arm of an immunoglobulin comprises two domains referred to as a $V_{H+L}$ region, and a $C_{H+L}$ region. As used herein, the term "variable region" or "V region" refers to a $V_{H+L}$ region, a $V_L$ region or a $V_H$ region. Also as used herein, the term "constant region" or "C region" refers to a $C_{H+L}$ region, a $C_L$ region or a $C_H$ region.

Limited digestion of an immunoglobulin with a protease produces two fragments. An antigen binding protease fragment is referred to as an Fab or an $F(ab')_2$ fragment. A protease fragment lacking the ability to bind to antigen is referred to as an Fc fragment. An Fab fragment comprises one arm of an immunoglobulin molecule containing a L chain ($V_L$ region+$C_L$ region) paired with the $V_H$ region and a portion of the $C_H$ region (CH1 domain). An $F(ab')_2$ fragment corresponds to two di-sulfide bonded arms of an immunoglobulin molecule, each arm containing a L chain ($V_L$ region+$C_L$ region) paired with a $V_H$ region and a CH1 domain.

A $C_H$ region defines the isotype of an immunoglobulin and confers different functional characteristics depending upon the isotype. For example, μ C regions enable the formation of pentameric aggregates of IgM molecules and α C regions enable the formation of dimers.

The antigen specificity of an immunoglobulin molecule is conferred by the amino acid sequence of a V region. As such, V regions of different immunoglobulin molecules can vary significantly depending upon their antigen specificity. Certain portions of a V region are invariant and are referred to as framework regions (FW regions). In contrast, certain portions of a V region are highly variable and are designated hypervariable regions. When the $V_L$ and $V_H$ domains pair in an immunoglobulin molecule, the hypervariable regions from each domain associate and create hypervariable loops that form antigen binding sites. Thus, the hypervariable loops determine the specificity of an immunoglobulin and are termed complementarity-determining regions (CDRs) because their surfaces are complementary to antigens.

Further variability of V regions is conferred by combinatorial variability of gene segments that encode an immunoglobulin V region. Immunoglobulin genes comprise multiple germline gene segments which somatically rearrange to form a rearranged immunoglobulin gene that encodes an immunoglobulin molecule. $V_L$ regions are encoded by a L chain V gene segment and J gene segment (joining segment). $V_H$ regions are encoded by a H chain V gene segment, D gene segment (diversity segment) and J gene segment (joining segment).

Figure 3:
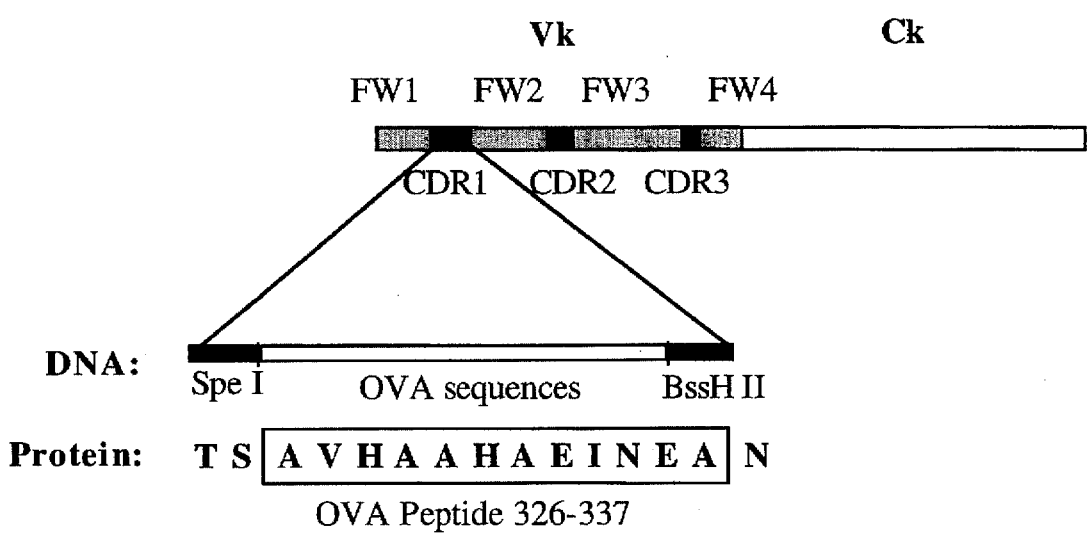

Both a L chain and H chain V gene segment contains three regions of substantial amino acid sequence variability. Such regions are referred to as L chain CDR1, CDR2 and CDR3, and H chain CDR1, CDR2 and CDR3, respectively. The length of an L chain CDR1 can vary substantially between different $V_L$ regions. For example, the length of CDR1 can vary from about 7 amino acids to about 17 amino acids. In contrast, the lengths of L chain CDR2 and CDR3 typically do not vary between different $V_L$ regions. The length of a H chain CDR3 can vary substantially between different $V_H$ regions. For example, the length of CDR3 can vary from about 1 amino acid to about 20 amino acids. In contrast, the lengths of H chain CDR1 and CDR2 typically do not vary between different $V_H$ regions. Each H and L chain CDR region is flanked by FW regions. FIG. 3 illustrates the organization of the CDR regions and FW region of a $V_L$ region having three CDRs.

Other functional aspects of an immunoglobulin molecule include the valency of an immunoglobulin molecule, the affinity of an immunoglobulin molecule, and the avidity of an immunoglobulin molecule. As used herein, affinity refers to the strength with which an immunoglobulin molecule binds to an antigen at a single site on an immunoglobulin molecule (i.e., a monovalent Fab fragment binding to a monovalent antigen). Affinity differs from avidity which refers to the sum total of the strength with which an immunoglobulin binds to an antigen. Immunoglobulin binding affinity can be measured using techniques standard in the art, such as competitive binding techniques, equilibrium dialysis or BIAcore methods. As used herein, valency refers to the number of different molecules an immunoglobulin molecule can combine with at one time. For example, a monovalent immunoglobulin molecule can only bind to one antigen at one time, whereas a bivalent immunoglobulin molecule can bind to two or more antigens at one time, and so forth.

Embodiments of the present invention include an immunoglobulin fusion protein comprising an immunoglobulin molecule associated with, such as by being linked to, a peptide precursor. As used herein, the term immunoglobulin molecule refers to at least a portion of a complete (e.g., full) immunoglobulin molecule which has functional aspects of that immunoglobulin molecule. For example, the term refers to a portion of an immunoglobulin molecule capable of forming a functional antigen binding site such that the immunoglobulin molecule binds to the antigen in the presence of antigen under conditions in which a complete immunoglobulin molecule would bind to an antigen. The immunoglobulin molecule of the immunoglobulin fusion protein of the present invention comprises at least one CDR region, and preferably, at least one arm having all naturally occurring CDR regions of that arm.

In embodiments of the present invention, an immunoglobulin molecule of the immunoglobulin fusion protein comprises at least a portion of an immunoglobulin C region. Suitable $C_L$ and $C_H$ regions for use with an immunoglobulin fusion protein of the present invention include κ, λ, μ, γ1, γ2, γ2a, γ2b, γ3, γ4, α, α1, α2, δ and ε constant regions, with human κ, λ, μ, γ1, γ2, γ3, γ4, α1, α2, δ and ε constant regions being more preferred. In some embodiments, an immunoglobulin fusion protein comprises an Fab fragment, an F(ab')$_2$ fragment, an Fc fragment, or Fab, F(ab')$_2$ or Fc fragments having amino acid residues inserted, substituted or deleted in such a manner that the fragments maintain functional activity (i.e., antigen binding).

An immunoglobulin fusion protein of the present invention contains a peptide precursor which comprises at least a portion of an antigen, wherein at least a portion of such peptide precursor is capable of effecting an immune response. Such antigens, for example, are ones with which it is desired to regulate an immune response. For example, peptide precursor which in the context of an MHC molecule, can bind to a TCR and effect a T cell response. A peptide precursor of the present invention is associated with an immunoglobulin molecule in such a manner that the peptide precursor does not substantially interfere with desired binding interactions by an arm of the immunoglobulin molecule and that the peptide precursor can be recognized by a TCR after the peptide precursor is processed (i.e., cleaved from the immunoglobulin in such a manner that at least a portion of the peptide precursor can bind to an MHC molecule). As used herein, the term "associated" refers to covalently attaching a peptide precursor to an immunoglobulin molecule by, for example, chemical cross-linking or peptide bonding using recombinant DNA technology. Chemical cross-linking can be achieved by methods including glutaraldehyde linkage, photoaffinity labelling, treatment with carbodiimides, treatment with chemicals capable of linking di-sulfide bonds, and treatment with other cross-linking chemicals standard in the art.

According to the present invention, a peptide precursor can be associated to any portion of an immunoglobulin molecule. Preferably, a peptide precursor of the present invention is associated with a V region of an immunoglobulin molecule. More preferably, a peptide precursor is associated with a CDR domain of a V region of an immunoglobulin molecule (ass illustrated in FIG. 1). Even more preferably, a peptide precursor is associated with a L chain CDR domain. In a preferred embodiment, a peptide precursor is associated with a CDR1 domain of a $V_L$ region of an immunoglobulin molecule.

One embodiment of a peptide precursor of the present invention comprises a polypeptide capable of being internally hydrolyzed from the immunoglobulin fusion protein into one or more antigenic peptides capable of binding to an MHC molecule in such a manner that the MHC-peptide complex can bind to TCR and effect a T cell response. For the purposes of the present invention, a polypeptide useful as a peptide precursor refers to a sequence of amino acid residues greater than 40 amino acids. In contrast, an antigenic peptide of the present invention refers to a sequence of amino acid residues of no more than 40 amino acids. When the peptide precursor is a polypeptide, it can be processed by internal hydrolysis within an APC by hydrolysis at two sites, thereby creating a single peptide; or by hydrolysis at three sites, thereby creating two peptides; or etc.

A preferred polypeptide to be inserted into an immunoglobulin molecule as a polypeptide precursor of the present invention has a molecular weight of at least about 40 kD. A more preferred polypeptide has a molecular weight of at least about 1.5 kD. An even more preferred polypeptide has a molecular weight of at least about 0.7 kD.

In another embodiment, a peptide precursor of the present invention comprises an antigenic peptide. Suitable antigenic peptides of the present invention comprise MHC class II restricted peptides (i.e., peptides capable of binding to MHC class II molecules). A suitable length of an antigenic peptide of the present invention ranges from about 5 to about 40 amino acid residues, more preferably from about 9 to about 30 amino acid residues, and even more preferably from about 12 to about 18 amino acid residues. A peptide precursor of the present invention can be selected such that use of such a peptide precursor regulates an immune response to antigenic proteins selected from: antigenic proteins synthesized inside of a cell; antigenic proteins synthesized outside of a cell; antigenic proteins hydrolyzed inside of a cell; or antigenic proteins hydrolyzed outside of a cell. In particular, a peptide precursor of the present invention can be selected such that use of such a peptide precursor regulates an immune response to antigenic proteins selected from: autoantigens, antigens derived from infectious agents, toxins, allergens, or mixtures thereof.

Preferred autoantigens of the present invention include, but are not limited to, at least a portion of a thyroid-stimulating hormone receptor, pancreatic β cell antigens, epidermal cadherin, acetyl choline receptor, platelet antigens, nucleic acids, nucleic acid:protein complexes, myelin protein, thyroid antigens, joint antigens, antigens of the nervous system, salivary gland proteins, skin antigens, kidney antigens, heart antigens, lung antigens, eye antigens, erythrocyte antigens, liver antigens and stomach antigens.

Preferred toxins of the present invention include, but are not limited to, staphylococcal enterotoxins, toxic shock syndrome toxin, retroviral antigens, streptococcal antigens, mycoplasma, mycobacterium, and herpes viruses. Retroviral antigens include antigens derived from human immunodeficiency virus. Even more preferred toxins include staphylococcal enterotoxin-A (SEA), staphylococcal enterotoxin-B (SEB), staphylococcal enterotoxin$_{1-3}$ (SE$_{1-3}$), staphylococcal enterotoxin-D (SED), and staphylococcal enterotoxin-E (SEE).

Preferred infectious agents of the present invention include, but are not limited to, bacteria, viruses, yeast, animal parasites and fungi. Preferred animal parasites include protozoan parasites, helminth parasites (such as nematodes, cestodes, trematodes, ectoparasites and fungi).

Preferred allergens of the present invention include, but are not limited to plant pollens, drugs, foods, venoms, insect excretions, molds, animal fluids, and animal hair and dander.

Preferred plant pollens include, but are not limited to, ragweed, trees, grass, flowers and ferns. Preferred drugs include, but are not limited to, penicillin, sulfonamides, local anesthetics, salicylates, serum, and vaccines. Preferred foods include, but are not limited to, nuts, seafood, eggs, peas, beans and grain products. Preferred venoms include, but are not limited to, bee venom, wasp venom, ant venom, and snake venom. Preferred insect secretions comprise proteins released by an insect during feeding. Preferred animal excretions include, but are not limited to, urine and saliva.

Preferred antigenic peptides of the present invention include peptides identified in Tables 1 and 3 in Rothbard et al., pp. 527–565, 1991, Ann. Rev. Immunol., Vol. 9, which is incorporated herein by reference. The amino acid sequences of such peptides can vary by addition, subtraction or substitution of amino acid residues, such that the variations do not effect the ability of the peptide to bind to an MHC molecule in such a manner that the peptide:MHC complex is recognized by a TCR.

Particularly preferred antigenic peptides of the present invention include at least a portion of ovalbumin or acetyl choline receptor. Preferred embodiments of antigenic peptides of the present invention include OVA peptide 326–337, OVA peptide 323–340, AChR peptide 146–162, or AChR peptide 111–126.

Embodiments of the present invention include an immunoglobulin fusion protein capable of binding to an antigen on the surface of an antigen presenting cell (APC) for the purpose of immunomodulating an immune response by targeting a specific peptide precursor to a specific APC. As used herein, an antigen refers to any compound capable of binding to an immunoglobulin. As such, antigens include, for example, proteins and carbohydrate moieties. It should be noted that, an antigen on the surface of an APC differs from an antigenic peptide of the present invention in that an antigenic peptide refers to an amino acid sequence capable of binding to an MHC molecule in such a manner that the antigenic peptide is recognized by a TCR (discussed in detail above). The purpose of binding an immunoglobulin fusion protein to an antigen on the surface of an APC is to deliver a peptide precursor (e.g., an antigenic peptide) to the APC. Suitable APC antigens include antigens on the surface of dendritic cells, macrophages and B lymphocytes (cells). Preferred APC antigens include, but are not limited to, a class II molecule, membrane-bound IgM, membrane-bound IgD, membrane-bound IgA, B7, B7-2, CD10, CD11c, CD13, CD19, CD22, CD33, CD35, CD38, CD40, CD45, CD45R, MAC-1, LFA-3, ICAM-1, ICAM-2, ICAM-3, VLA-4, CD22, 33D1, R4/23, F4/80, and KiM4.

Preferred immunoglobulin fusion proteins of the present invention that are capable of binding to an antigen on the surface of an APC include, but are not limited to: M3/38, a rat IgG2a antibody specific for MAC-2 antigen on macrophages; JA12.5, a rat IgG2a antibody specific for membrane-bound IgD found mainly on the surface of a non-professional B cell; MKD6, a rat IgG2a antibody specific for IA$^d$; and SFRS-B6, a rat IgG2a antibody specific for human class I HLA-Bw6.

In one embodiment, an immunoglobulin fusion protein of the present invention comprises an immunoglobulin molecule linked to a peptide precursor, wherein the immunoglobulin molecule comprises a variable region capable of binding to an antigen on the surface of an antigen presenting cell. As used herein, the term "linked" refers to attaching a peptide precursor to an immunoglobulin molecule by peptide bonds between the carboxyl end (COOH termini) of a first amino acid sequence and the amino end (NH2 termini) of a second amino acid sequence or to either a carboxyl and/or an amino terminal portion of an immunoglobulin molecule. Prior to the development of a novel recombinant immunoglobulin fusion protein of the present invention, some chimeric immunoglobulin:antigen complexes suffered from unpredictable association of antigen with immunoglobulin. In particular, immunoglobulin:antigen complexes derived from in vitro chemical cross-linking suffer unpredictability problems because the quality and the quantity of antigen being cross-linked to an immunoglobulin. The unpredictability of immunoglobulin:antigen complexes limits the use of the complexes as reliable reagents for medical and/or experimental use. The method of linking a peptide precursor to an immunoglobulin molecule as in the present invention alleviates such problems and allows for the production of immunoglobulin fusion protein that are uniquely suitable for use as therapeutic and experimental agents.

A preferred immunoglobulin fusion protein contains a peptide precursor linked by a recombinantly produced (e.g., by translation of a nucleic acid molecule) peptide bond. A peptide precursor of the present invention can be attached to an immunoglobulin molecule by being substituted in (i.e., a peptide precursor does replace certain immunoglobulin molecule residues) into an immunoglobulin molecule, being inserted in (i.e., a peptide precursor does not replace any immunoglobulin molecule residues), or by being linked to the end of an immunoglobulin chain. Preferably, a peptide precursor is substituted into an immunoglobulin molecule.

In another embodiment, an immunoglobulin fusion protein of the present invention comprises an immunoglobulin molecule associated with a peptide precursor, wherein the immunoglobulin molecule is capable of binding to an antigen that distinguishes between types of antigen presenting cells. An immunoglobulin fusion protein capable of distinguishing between types of APCs is particularly advantageous because different types of APCs are involved in different immune disorders. For example, regulation of T cell activity by dendritic cells can effect the progression of AIDS more than regulation of T cell activity by macrophages. Preferred APC antigens useful for distinguishing between types of APCs include, a membrane-bound IgM, membrane-bound IgD, membrane-bound IgA, CD45R, CD22, CD13, CD33, F4/80, 33D1, R4/23. KiM4, CD35, B7-2, CD11c, and MHC class II.

In other embodiments of the present invention, an immunoglobulin fusion protein is capable of binding to an antigen on the surface of a non-professional APC and a professional APC. According to the present invention, professional and non-professional APC's are defined as follows. The activity of T lymphocytes (cells) is regulated by TCR binding to MHC molecules complexed with antigenic peptide. Without being bound by theory, it is believed that the activity of a T cell can also be controlled by the interaction between other effector molecules on the surface of APCs and T cells. The interaction of such effector molecules can cause a T cell to be stimulated, anergized or killed. Activation of a T cell refers to induction of signal transduction pathways in the T cell resulting in production of cellular products (e.g., interleukin-2) by that T cell. Anergy refers to the diminished reactivity by a T cell to an antigen. Effector molecules involved in T cell activation include, but are not limited to, B7, B7-2, CD28, CD40 and the CD40 ligand. APCs having B7 or B7-2, and CD40 are capable of activating T cells by binding to CD28 and CD40 ligand, respectively, on the surface of a T cell. Such APCs are referred to as professional APCs. APCs lacking B7 or B7-2, and/or CD40 are capable of anergizing naive T cells (T cells that have never been activated). Such APCs are referred to as non-professional APCs.

Preferred professional APC-specific immunoglobulin fusion proteins of the present invention are capable of binding to an antigen on the surface of dendritic cells, macrophages and B cells that express B7, B7-2 and CD40. Preferred non-professional APC-specific immunoglobulin fusion protein of the present invention are capable of binding to an antigen on the surface of dendritic cells, macrophages and B cells that do not express B7, B7-2 and CD40. More preferred non-professional APC-specific immunoglobulin fusion protein are capable of binding to an antigen on the surface of B cells that do not express B7 and/or B7-2.

In other embodiments of the present invention, an immunoglobulin fusion protein is capable of binding to an antigen on the surface of an APC capable of activating a $T_H1$ or a $T_H2$ cell. According to the present invention, a $T_H2$ cell is a T cell that is capable of stimulating antibody production by secreting cytokines, such as IL-10 and TGF-$\beta$. $T_H2$ cells differ from $T_H1$ cells which promote inflammation by secreting cytokines which activate macrophages.

Other embodiments of the present invention include a soluble immunoglobulin fusion protein. Soluble immunoglobulin fusion proteins of the present invention include immunoglobulin fusion protein that are not contained in a lipid-containing substrate. A secreted immunoglobulin fusion protein can be produced using an immunoglobulin $C_H$ region that lacks sufficient amino acid sequences capable of anchoring the molecule into a lipid-containing substrate, such as an immunoglobulin transmembrane domain and/or an immunoglobulin cytoplasmic domain. A soluble form of an immunoglobulin fusion protein of the present invention is advantageous because the immunoglobulin fusion protein can be easily delivered to and phagocytozed by an APC.

In another embodiment, an immunoglobulin fusion protein is capable of being bound by a lipid-containing substrate, preferably by a plasma membrane of a cell that produces the immunoglobulin fusion protein. As used herein, the term "anchoring" refers to the insertion of a protein in a lipid-containing substrate such that any extracellular domains are on the outside of the substrate. An immunoglobulin fusion protein of the present invention capable of being bound by a lipid-containing substrate is referred to herein as a membrane-bound immunoglobulin fusion protein. An immunoglobulin $C_H$ region useful in the production of a membrane-bound immunoglobulin fusion protein can include any amino acid sequence capable of anchoring a protein into a lipid-containing substrate combined with the extracellular domains of the immunoglobulin protein. Preferably, the $C_H$ region contains at least one immunoglobulin transmembrane domain and at least a portion of at least one immunoglobulin cytoplasmic domain. A membrane-bound immunoglobulin fusion protein is particularly advantageous because immunoglobulin fusion proteins can be co-delivered with other useful reagents such as cytokines, toxins and enzymes.

The immunoglobulin fusion proteins of the present invention can either be in the form of single immunoglobulin molecular units (i.e., two L chains and two H chains bound by di-sulfide bonds) or in multimeric units, wherein multiple single immunoglobulin molecular units are joined together. The term "meric unit" will be used to refer to a single immunoglobulin molecular unit and terms such as "dimer," "trimer," and so forth will be used to refer to multimeric units. It should be recognized that meric units can either be "heteromeric" or "homomeric." The term heteromeric refers to a meric unit in which only one arm of the meric unit is capable of binding to an antigen. As such, a heteromeric unit can have a first arm associated with a peptide precursor that disrupts the antigen binding ability of the arm, and a second arm that is associated with a peptide precursor that does not disrupt antigen binding ability or a second arm that is not associated with a peptide precursor. The term homomeric refers to a meric unit in which both arms of the meric unit are capable of binding to an antigen. As such, a homomeric unit can have one arm or two arms associated with a peptide precursor that does not disrupt the antigen binding ability of the associated arm. Illustrations of a homomeric immunoglobulin fusion protein of the present invention include a $V_{Lpep^*}\text{-}V_H/V_L\text{-}V_H$; $V_L\text{-}V_{Hpep^*}/V_L\text{-}V_H$; or $V_{Lpep^*}\text{-}V_{Hpep^*}/V_L\text{-}V_H$, wherein "pep*" refers to a peptide precursor of the present invention that does not interfere with the antigen binding ability of the immunoglobulin arm to which the peptide precursor is attached. Illustrations of a heteromeric immunoglobulin fusion protein of the present invention include a $V_{Lpep^*}\text{-}V_H/V_{Lpep}\text{-}V_H$; $V_{Lpep^*}\text{-}V_H/V_L\text{-}V_{Hpep}$; $V_L\text{-}V_{Hpep}/V_{Lpep}\text{-}V_H$; $V_L\text{-}V_{Hpep^*}/V_L\text{-}V_{Hpep}$; $V_{Lpep^*}\text{-}V_{Hpep^*}/V_{Lpep}\text{-}V_H$; $V_{Lpep^*}\text{-}V_{Hpep^*}/V_L\text{-}V_{Hpep}$; and $V_{Lpep^*}\text{-}V_{Hpep^*}/V_{Hpep}\text{-}V_{Hpep}$, wherein "pep" refers to a peptide precursor of the present invention that does interfere with the antigen binding ability of the immunoglobulin arm to which the peptide precursor is attached.

Individual immunoglobulin fusion proteins of the present invention can be assembled into multimeric immunoglobulin fusion protein complexes comprising dimers, trimers, tetramers or pentamers, with dimers and pentamers being more preferred. Such multimeric immunoglobulin fusion protein complexes can be formed using protein conjugation methods known to those of skill in the art, including chemical cross-linking or recombinant DNA technology. Preferred dimeric immunoglobulin fusion protein complexes of the present invention comprise immunoglobulin fusion proteins having IgG, IgA, IgE C regions which naturally form dimeric structures. Preferred pentameric immunoglobulin fusion protein complexes of the present invention comprise immunoglobulin fusion proteins having μ C regions which naturally form pentameric structures.

In the case of multimeric immunoglobulin fusion protein complexes, each immunoglobulin fusion protein can be the same or different. For example, each immunoglobulin fusion protein can be either a heteromeric unit or a homomeric unit. In addition, each immunoglobulin fusion protein can contain the same or different peptide precursors. Further, some units in a multimeric structure can be naturally occurring-immunoglobulin molecules which are not fusion proteins.

Another aspect of the present invention relates to a nucleic acid molecule that encodes the immunoglobulin fusion protein disclosed herein or a portion thereof. A nucleic acid molecule can be DNA, RNA, or hybrids or derivatives of either DNA or RNA. Nucleic acid molecules of the present invention can include regulatory regions that control expression of the nucleic acid molecule (e.g., transcription or translation control regions), full-length or partial coding regions, and combinations thereof. Any portion of a nucleic acid molecule of the present invention can be produced by: (1) isolating the molecule from its natural milieu; (2) using recombinant DNA technology (e.g., PCR amplification, cloning); or (3) using chemical synthesis methods.

A nucleic acid of the present invention can include portions which are functional equivalents of natural nucleic acid molecules encoding an immunoglobulin molecule or portions thereof, or a peptide precursor, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode at least a portion of a protein of the present invention capable of forming an immunoglobulin fusion protein which is capable of delivering a peptide precursor in such a manner that at least a portion of the peptide precursor binds to an MHC class II molecule and can be recognized by a TCR. Preferred functional equivalents include sequences capable of hybridizing under stringent conditions, to at least a portion of an immunoglobulin fusion protein encoding nucleic acid molecule (according to conditions described in Sambrook et al., *Molecular Cloning: A Laboratory Manual*, Cold Spring Harbor Labs Press, 1989, which is incorporated herein by reference in its entirety). As guidance in determining what particular modifications can be made to any particular nucleic acid molecule, one of skill in the art should consider several factors that, without the need for undue experimentation, permit a skilled artisan to appreciate workable embodiments of the present invention. For example, such factors include modifications to nucleic acid molecules done in a manner so as to maintain particular functional regions of the encoded proteins including, regions needed for inter-chain association between immunoglobulin H and L chains, a working antigen binding site and a peptide precursor that does not substantially interfere with desired binding interactions by an arm of the immunoglobulin and that can be recognized by a TCR after the peptide precursor is processed (i.e., cleaved from the immunoglobulin in such a manner that at least a portion of the peptide precursor can bind to an MHC molecule). Functional tests for these various characteristics (e.g., binding studies) allows one of skill in the art to determine what modifications to nucleic acid sequences would be appropriate and which would not.

A nucleic acid molecule of the present invention comprises at least one nucleic acid sequence encoding a peptide precursor covalently attached (by base pair linkage) to at least one nucleic acid sequence encoding an immunoglobulin molecule, or a portion thereof. The nucleic acid sequences are attached in such a manner that the peptide precursor and immunoglobulin molecule sequences are transcribed in-frame, thereby producing a functional immunoglobulin fusion protein or a portion thereof, capable of forming an antigen binding site, alone or in combination with another immunoglobulin chain.

A preferred nucleic acid molecule of the present invention encodes an immunoglobulin $V_H$ region, $C_H$ region, $V_L$ region, $C_L$ region, and a peptide precursor; an immunoglobulin $V_H$ region, $V_L$ region, $C_L$ region, CH1 domain, and a peptide precursor; or an immunoglobulin $V_L$ region, $C_L$ region, and a peptide precursor. A particularly preferred nucleic acid molecule encodes an immunoglobulin $V_L$ region, $C_L$ region and a peptide precursor. Thus, it should be recognized that the nucleic acid molecules of the present invention can encode for one or more chains of an immunoglobulin fusion protein of the present invention.

A portion of each nucleic acid molecule encoding a component (i.e., an immunoglobulin molecule or a peptide precursor) of an immunoglobulin fusion protein chain can be covalently associated (using standard recombinant DNA methods) to any other nucleic acid molecule portion encoding a distinct component to produce an immunoglobulin fusion protein of the present invention, or portion thereof. A nucleic acid sequence encoding a peptide precursor is preferably covalently associated (by base pair linkage, e.g., ligated) to a nucleic acid molecule encoding a portion of an immunoglobulin molecule. In one embodiment, a nucleic acid molecule encoding for a peptide precursor of the present invention is covalently associated with a nucleic acid molecule encoding for an immunoglobulin by ligating the 3' end (end encoding the C-terminus) of a nucleic acid molecule encoding a FW1 domain of a $V_L$ region of an immunoglobulin to the 5' end (end encoding the N-terminus) of a nucleic acid molecule encoding a peptide precursor of the present invention and ligating the 3' end of the nucleic acid molecule encoding the peptide precursor to the 5' end of a nucleic acid molecule encoding a FW2 domain of the $V_L$ region.

In another embodiment, a nucleic acid molecule encoding for a peptide precursor of the present invention is covalently associated with a nucleic acid molecule encoding for an immunoglobulin by ligating the 3' end (end encoding the C-terminus) of a nucleic acid molecule encoding a FW2 domain of a $V_H$ region of an immunoglobulin to the 5' end (end encoding the N-terminus) of a nucleic acid molecule encoding a peptide precursor of the present invention and the 3' end of the nucleic acid molecule encoding the peptide precursor to the 5' end of a nucleic acid molecule encoding a FW3 domain of the $V_H$ region.

In yet another embodiment, a nucleic acid molecule encoding for a peptide precursor of the present invention is covalently associated with a nucleic acid molecule encoding for an immunoglobulin by ligating the 3' end (end encoding the C-terminus) of a nucleic acid molecule encoding a FW3 domain of a $V_H$ region of an immunoglobulin to the 5' end (end encoding the N-terminus) of a nucleic acid molecule encoding a peptide precursor of the present invention and the 3' end of the nucleic acid molecule encoding the peptide precursor to the 5' end of a nucleic acid molecule encoding a FW4 domain of the $V_H$ region.

In some embodiments of the nucleic acid molecules of the present invention can also include a nucleic acid sequence that encodes for a signal or leader segment that is capable of promoting secretion of a immunoglobulin fusion protein from the cell that produces the protein. Nucleic acid sequences encoding such leader or signal segments are covalently associated (by base pair linkage) to the 5' end of a nucleic acid molecule. The leader or signal segments can be segments which naturally are associated with an MHC segment or are heterologous. Preferred segments are naturally associated segments. To obtain membrane-bound embodiments, nucleic acid sequences of the present invention can include nucleic acid sequences which encode for at least one transmembrane segment capable of anchoring an immunoglobulin fusion protein to a lipid-containing substrate, such segments including at least a portion of an immunoglobulin transmembrane domain and at least a portion of an immunoglobulin cytoplasmic domain. A nucleic acid sequence encoding a transmembrane segment is covalently associated (by base pair linkage) to the 3' end of a nucleic acid sequence encoding the extracellular portion of an immunoglobulin fusion protein. The transmembrane segment can be a segment naturally associated with the immunoglobulin or heterologous. Preferred transmembrane segments include segments that are naturally associated with an immunoglobulin. A nucleic acid molecule encoding an immunoglobulin fusion protein or portion thereof capable of being membrane-bound contains at least one nucleic acid sequence encoding a segment ligated to the 3' end of an extracellular domain in a manner such that the transmembrane encoding sequence is transcribed in-frame.

A preferred nucleic acid molecule of the present invention comprises a nucleic acid molecule having a sequence encoding an immunoglobulin light chain linked to a peptide precursor, wherein the immunoglobulin light chain is capable binding to a molecule on the surface of an antigen presenting cell when associated with a compatible immunoglobulin heavy chain. Particularly preferred nucleic acid molecules of the present invention include: $V_\kappa$-$OVA_{326-337}$ having sequences encoding an ovalbumin (326–337) peptide and a L chain (described in detail in Example 1, illustrated in FIG. 2); $V_\kappa$-$OVA_{323-340}$ having sequences encoding an ovalbumin (323–340) peptide and a L chain (described in detail in Example 4); $V_\kappa$-$AChR_{146-162}$ and a L chain having sequences encoding the acetyl choline receptor (146–162) peptide (described in detail in Example 3); or $V_\kappa$-$AChR_{111-126}$ having sequences encoding the acetyl choline receptor (111–126) peptide (described in detail in Example 3).

In one embodiment, an immunoglobulin molecule of an immunoglobulin fusion protein of the present invention is derived from (i.e., encoded by a nucleic acid molecule isolated from) an animal. An immunoglobulin molecule can be derived from the same species of animal to which the immunoglobulin molecule is to be administered, or a different species. If the immunoglobulin molecule is derived from a different species, then preferably the immunoglobulin fusion protein is derived from a species that does not induce a substantial immune response against the administered immunoglobulin molecule. Further, it is within the scope of the invention that different portions of an immunoglobulin molecule can be derived from different species of animals. For example, an immunoglobulin molecule of the present invention can comprise a mouse V region and a human C region, and so forth. A preferred immunoglobulin molecule is derived from animals including, but not limited to, humans, mice, rats, hamsters, or mixtures thereof, a more preferred immunoglobulin molecule is derived from humans, mice, or mixtures thereof, and an even more preferred immunoglobulin molecule is derived from humans.

The present invention also includes a recombinant molecule comprising a nucleic acid molecule of the present invention operatively linked to a vector capable of being expressed in a host cell. As used herein, "operatively linked" refers to insertion of a nucleic acid sequence into an expression vector in such a manner that the sequence is capable of being expressed when transformed into a host cell. As used herein, an "expression vector" is an RNA or DNA vector capable of transforming a host cell and effecting expression of an appropriate nucleic acid sequence, preferably replicating within the host cell. An expression vector can be either prokaryotic or eukaryotic, and typically is a virus or a plasmid.

Construction of desired expression vectors can be performed by methods known to those skilled in the art and expression can be in eukaryotic or prokaryotic systems. Procaryotic systems typically used are bacterial strains including, but not limited to various strains of *E. coli*, various strains of *bacilli* or various species of Pseudomonas. In prokaryotic systems, plasmids are used that contain replication sites and control sequences derived from a species suitable for use with a host cell. Control sequences can include, but are not limited to promoters, operators, enhancers, ribosome binding sites, and Shine-Dalgarno sequences. Expression systems useful in eukaryotic host cells comprise promoters derived from appropriate eukaryotic genes. Useful mammalian promoters include early and late promoters from SV40 or other viral promoters such as those derived from baculovirus, polyoma virus, adenovirus, bovine papilloma virus or avian sarcoma virus. Expression vectors of the present invention include any vectors that function (i.e., direct gene expression) in recombinant cells of the present invention including bacterial, yeast, other fungal, insect, and mammalian cells. Preferred expression vectors of the present invention include vectors containing immunoglobulin H chain promoters and/or L chain promoters, in particular kappa promoters. Useful mammalian enhancers include immunoglobulin H chain enhancers and/or L chain enhancers, in particular kappa enhancers. Particularly preferred expression vectors for use with the present invention include pJO11 and pJHuCK.

An expression system can be constructed from any of the foregoing control elements operatively linked to the nucleic acid sequences of the present invention using methods known to those of skill in the art. (see, for example, Sambrook et al., ibid.).

Recombinant molecules of the present invention include nucleic acid molecules of the present invention encoding a peptide precursor linked to an immunoglobulin molecule, as disclosed herein. Preferred recombinant molecules of the present invention include $pV_\kappa$-$OVA_{326-337}$ (described in detail in Example 1); $pV_\kappa$-$OVA_{323-340}$ (described in detail in Example 4); $pV_\kappa$-$AChR_{146-162}$ (described in detail in Example 3); and $V_\kappa$-$AChR_{111-126}$ (described in detail in Example 3).

Host cells of the present invention can be cells naturally capable of producing immunoglobulin protein, or cells that are capable of producing immunoglobulin molecule when transfected with a nucleic acid molecule encoding an immunoglobulin molecule. Host cells of the present invention include, but are not limited to bacterial, fungal, insect and mammalian cells. Suitable host cells include mammalian cells capable of producing an immunoglobulin molecule, preferably B cells including splenic B cells, lymph node B cells, myeloma cells and hybridoma cells. Hybridoma cells refer to hybrid cell lines comprising myeloma cells (tumor cells capable of being maintained in tissue culture but do not produce immunoglobulin) fused with, for example, a spleen cell capable of producing an immunoglobulin molecule.

All embodiments of a host cell are capable of producing heterologous immunoglobulin chain which includes a peptide precursor. In addition, all embodiments of a host cell of the present invention are selected from cells which include: a cell capable of producing a heterologous immunoglobulin molecule but does not produce an endogenous immunoglobulin molecule; a cell expressing a heterologous H and/or L chain; or a cell capable of producing an endogenous immunoglobulin H chain; a cell capable of producing an endogenous H and L chain, wherein the H and L chains are compatible. As used herein, compatible chains refer to distinct immunoglobulin chains that are capable of associating in such a manner that the chains form functional immunoglobulin V regions and/or C regions.

A preferred host cell of the present invention comprises a cell capable of producing an endogenous immunoglobulin molecule capable of binding to an antigen on the surface of an APC (as disclosed herein). In a preferred embodiment, host cells of the present invention include, but are not limited to, cells having the American Type Culture Collection identification number HB44, TIB128, HB61, HB70, HB149, HB135, CRL1581 or CRL1580.

The present invention is also directed to a recombinant cell which can produce an immunoglobulin fusion protein of the present invention and which comprises a host cell transformed with one or more recombinant molecules of the present invention. Suitable recombinant cells of the present invention include recombinant cells producing an immunoglobulin fusion protein comprising heterologous nucleic acid sequence encoding an immunoglobulin fusion protein, or preferably, recombinant cells producing an immunoglobulin fusion protein comprising heterologous and endogenous nucleic acid sequences encoding an immunoglobulin fusion protein.

One embodiment of a recombinant cell of the present invention comprises a host cell capable of producing endogenous immunoglobulin H chain, transformed with a recombinant molecule encoding a peptide precursor linked to an immunoglobulin L chain. The immunoglobulin H chain is capable of associating with the transformed L chain to form an immunoglobulin fusion protein of the present invention. The recombinant cell can be co-transformed with a recombinant molecule encoding a peptide precursor linked to an immunoglobulin H chain substantially similar to the endogenous H chain.

Another embodiment of a recombinant cell of the present invention comprises a host cell capable of producing endogenous immunoglobulin L chain, transformed with a recombinant molecule encoding a peptide precursor linked to an immunoglobulin H chain. The immunoglobulin L chain is capable of associating with the transformed H chain to form an immunoglobulin fusion protein of the present invention. The recombinant cell can be co-transformed with a recombinant molecule encoding a peptide precursor linked to an immunoglobulin L chain substantially similar to the endogenous L chain.

Another embodiment of a recombinant cell of the present invention comprises a host cell capable of producing endogenous immunoglobulin H and L chain, transformed with a recombinant molecule encoding a peptide precursor linked to an immunoglobulin H chain. The immunoglobulin L chain is capable of associating with the transformed H chain to form an immunoglobulin fusion protein of the present invention. The L chain is also capable of associating with the endogenous H chain. The recombinant cell can also be co-transformed with a recombinant molecule encoding a peptide precursor linked to an immunoglobulin L chain capable of associating with the endogenous and/or transformed H chain.

Another embodiment of a recombinant cell of the present invention comprises a host cell capable of producing endogenous immunoglobulin H and L chain, transformed with a recombinant molecule encoding a peptide precursor linked to an immunoglobulin L chain. The immunoglobulin H chain is capable of associating with the transformed L chain to form an immunoglobulin fusion protein of the present invention. The H chain is also capable of associating with the endogenous L chain, thereby enabling the cell to produce homomeric and heteromeric immunoglobulin fusion proteins. The recombinant cell can also be co-transformed with a recombinant molecule encoding a peptide precursor linked to an immunoglobulin H chain capable of associating with the endogenous and/or transformed L chain.

Preferred recombinant cells of the present invention include a recombinant cell having a recombinant molecule comprising a nucleic acid molecule operatively linked to an expression vector, the nucleic acid molecule having a sequence encoding at least a portion of an immunoglobulin fusion protein of the present invention as disclosed herein. Particularly preferred recombinant cells of the present invention comprise: a 33D1 B cell hybridoma capable of producing endogenous 33D1 immunoglobulin H and L chain, transformed with the recombinant molecule $pV_K$-$OVA_{326-337}$; a 33D1 B cell hybridoma capable of producing endogenous 33D1 immunoglobulin H and L chain, transformed with the recombinant molecule $pV_K$-$OVA_{323-340}$; a B cell hybridoma capable of producing endogenous TIB128 (anti-macrophage cell antibody) immunoglobulin H and L chain, transformed with the recombinant molecule $pV_K$-$AChR_{146-162}$; a B cell hybridoma capable of producing endogenous 33D1 (anti-dendritic cell antibody) immunoglobulin H and L chain, transformed with the recombinant molecule $V_K$-$AChR_{111-126}$; and a B cell hybridoma capable of producing endogenous TIB128 (anti-macrophage cell antibody) immunoglobulin H and L chain, transformed with the recombinant molecule $V_K$-$AChR_{111-126}$.

One aspect of the present invention is a method for producing an immunoglobulin fusion protein, comprising the steps of: (1) culturing a cell transformed with a nucleic acid encoding a portion of an immunoglobulin fusion protein of the present invention to produce the immunoglobulin fusion protein; and (2) recovering the immunoglobulin fusion protein. Such transformed recombinant cells are cultured under conditions effective to produce such proteins, and recovering the proteins. Effective conditions to produce an immunoglobulin fusion protein include, but are not limited to appropriate culture media, bioreactor, temperature, pH and oxygen conditions. Depending on the expression vector used for production, resultant proteins can either remain within the recombinant cell, be retained on the outer surface of the recombinant cell, or be secreted into the culture medium. As used herein, the term "recovering" refers to collecting the culture medium containing the protein and/or recombinant cells. Recovery need not imply additional steps of separation or purification.

After recovery, an immunoglobulin fusion protein of the present invention can be purified using a variety of standard protein purification techniques such as, but not limited to, affinity chromatography, ion exchange chromatography, ammonium sulfate precipitation, filtration, centrifugation, electrophoresis, hydrophobic interaction chromatography, gel filtration chromatography, chromatofocusing, high pressure liquid chromatography and differential solubilization. Isolated immunoglobulin fusion proteins are preferably retrieved in substantially pure form. As used herein, "substantially pure" refers to a purity that allows for the effective use of the protein as a heretofore described immunogen, toleragen or regulatory reagent.

Soluble immunoglobulin fusion protein of the present invention can be purified using, for example, immunoaffinity chromatography using an antibody capable of binding to the C region of the immunoglobulin fusion protein or an antigen capable of binding to the V region of the immunoglobulin fusion protein. Immunoglobulin fusion proteins anchored in a lipid-containing substrate can be recovered by, for example, density gradient centrifugation techniques.

Immunoglobulin fusion protein of the present invention can also be produced by B cells isolated from a transgenic animal expressing a transgene comprising a recombinant molecule of the present invention. Suitable animals useful for the production of a transgenic animal capable of producing an immunoglobulin fusion protein of the present invention include animals already expressing a transgene encoding a human immunoglobulin molecule; or animals incapable of expressing endogenous immunoglobulin molecules capable of binding to antigens on the surface of APCs (i.e., such animals incapable of expressing endogenous immunoglobulin molecules are termed "knock-out" animals). Transgenic animals of the present invention can be produced using methods known by those of skill in the art. For example, a transgene can be introduced into an animal by injecting eggs isolated from an animal with a transgene and implanting the eggs into an animal. The animal possessing the transgene is then bred and the offspring tested for expression of the transgene. Offspring expressing the transgene are considered transgenic for the transgene. Preferred animals for producing a transgenic animal include mice, rats, rabbits and cows.

In one embodiment, a recombinant molecule encoding a peptide precursor linked to a human immunoglobulin L chain is introduced into an animal already expressing a transgene encoding for a human immunoglobulin H chain. The immunoglobulin L chain is capable of associating with the human H chain already expressed by the animal to form an immunoglobulin fusion protein of the present invention.

In another embodiment, a recombinant molecule encoding a peptide precursor linked to a human H or L chain is co-introduced with another recombinant molecule encoding the corresponding type of human immunoglobulin chain which lacks a peptide precursor, into an immunoglobulin molecule knock-out animal. The immunoglobulin L chain is capable of associating with the immunoglobulin H chain to form an immunoglobulin fusion protein of the present invention.

Immunoglobulin fusion proteins produced by transgenic animals can be recovered using conventional hybridoma production technology known to those of skill in the art. For example, a transgenic animal of the present invention can be immunized with the antigen capable of being bound by the immunoglobulin molecule encoded by the transgene. The spleen and/or lymph nodes of the immunized transgenic animal can then be removed and the cells fused with compatible myeloma cells. Immunoglobulin fusion proteins can then be recovered from the culture supernatant of the fused cells using methods described below.

Embodiments of the present invention comprise the use of an immunoglobulin fusion protein, as disclosed in the present invention, to regulate an immune response in an animal. Therapeutic reagents of the present invention are useful for administration to subjects to immunize subjects against, for example, infectious agents and tumor cells, and to tolerize subjects against, for example, autoantigens, allergens, engraftments, and agents perfused into subjects (i.e., blood factors and platelets). Regulation of an immune response can include modulating the activity of molecules typically involved in an immune response (e.g., antibodies, antigens, major histocompatibility molecules (MHC) and molecules co-reactive with MHC molecules). This process is particularly applicable for purposes of specific immunization and immunotolerance, and derives from the novel structure of an immunoglobulin fusion protein of the present invention. Immunization refers to stimulating an immune response by, for example, activating T helper cells to secrete cytokines which stimulate immunoglobulin production by B cells. Immunotolerance refers to inhibiting an immune response by, for example, killing or anergizing (i.e., diminishing reactivity by a T cell to an antigenic peptide) particular cells involved in the immune response. According to the present invention, an immunoglobulin fusion protein capable of inducing immunological unresponsiveness to an antigen in an animal is referred to as a "toleragen" and an immunoglobulin fusion protein capable of inducing an immune response in an animal is referred to as an "immunogen."

Effective immunogens typically mimic a natural infection by a foreign agent. As such, an immunogen is ideally delivered to an APC so that the immunogen may be complexed with an MHC molecule and presented to T cells on the surface of an APC as part of an MHC/immunogen complex. Traditional peptides and proteins when used as immunogenic agents by traditional delivery methods, however, are usually weakly immunogenic because of their inability to enter the cellular compartments of an APC for presentation to T cells. Usually adjuvants (e.g., Alum or Freund's adjuvant) are needed to improve the immunogenicity of an immunogen. Adjuvants, however, cause harmful side-effects such as fever and inflammation. An immunoglobulin fusion protein of the present invention provides for a novel immunogen that has the advantages of delivering a peptide precursor directly to an APC and can be effective in the absence of adjuvant. By delivering peptide precursors representative of antigens from infectious agents or tumor cells, immune responses can be induced that discriminate between specific antigens.

Traditional peptides and proteins when used as toleragenic agents also suffer from similar drawbacks as traditional immunogenic agents in that they are usually weakly toleragenic because of their inability to enter the cellular compartments of an APC. In addition, as described in detail above, it is believed that toleragens need to be presented to T cells by specific APC cells lacking effector molecules necessary for T cell activation. As such, an immunoglobulin fusion protein of the present invention provides for a novel toleragen that has the advantage of delivering a peptide precursor specifically to an APC capable of anergizing or killing a T cell. By delivering peptide precursors representative of autoantigens, allergens and graft antigens, immune responses against such antigens can be inhibited.

The ability of an immunoglobulin fusion protein of the present invention to function as an immunogen or a toleragen can be contingent upon the valency of the immunoglobulin fusion protein. Without being bound by theory, it is believed that a multivalent immunoglobulin molecule stimulates an immune response by cross-linking antigens on the surface of the APC, thereby causing the APC to express certain effector molecules which play a role in activating T cells. Conversely, it is believed that a monovalent immunoglobulin molecule can inhibit an immune response by not cross-linking antigens on the surface of an APC, thereby not causing the APC to express the effector molecules. It is also believed that the absence of the effector molecules causes a T cell to be anergized or killed, rather than merely not stimulated.

Other factors can also influence the effectiveness of an immunoglobulin fusion protein of the present invention as an immunogen or a toleragen. For example, the single site affinity (i.e., the binding affinity of one arm of an immunoglobulin fusion protein to an antigen) with which an immunoglobulin fusion protein binds to an antigen on the surface of an APC can effect an immunoglobulin fusion protein's ability to tolerize or immunize. An immunoglobulin fusion protein having a higher single site affinity for an antigen is preferred over an immunoglobulin fusion protein having a lower single site affinity. Preferably, the V region of an immunoglobulin fusion protein has a single site binding affinity of more than about $10^6 M^{-1}$, more preferably more than about $10^8 M^{-1}$, and even more preferably more than about $10^{10} M^{-1}$ for an antigen on the surface of an APC.

It is within the scope of the present invention that an immunoglobulin fusion protein can be selected based upon the valency and the affinity of the immunoglobulin fusion protein. A preferred immunogen of the present invention has a high single site antigen binding affinity and has sufficient avidity to cross-link two or more antigens on the surface of an APC. A preferred toleragen of the present invention has a high single site antigen binding affinity and has insufficient avidity to cross-link two or more antigens on the surface of an APC.

An immunogen of the present invention is capable of inducing an immune response by delivering a peptide precursor to an APC in such a manner that the APC is capable of activating a T cell. A preferred immunogen of the present invention comprises a multivalent immunoglobulin fusion protein capable of binding two or more antigens on the surface of an APC. Such immunogens can be monomeric or multimeric. Preferred V regions of an immunogen comprising a meric unit of the present invention include: $V_{Lpep*}$-$V_H/V_L$-$V_H$; $V_{Lpep*}$-$V_H/V_{Lpep*}$-$V_H$; $V_{Lpep*}$-$V_H/V_L$-$V_{Hpep*}$; $V_{Lpep*}$-$V_H/V_{Lpep*}$-$V_{Hpep*}$; $V_L$-$V_{Hpep*}/V_L$-VH; $V_L$-$V_{Hpep*}/V_{Lpep*}$-$V_H$; $V_L$-$V_{Hpep*}/V_L$-$V_{Hpep*}$; $V_L$-$V_{Hpep*}/V_{Lpep*}$-$V_{Hpep*}$; or $V_{Lpep*}$-$V_{Hpep*}/V_{Lpep*}$-$V_{Hpep*}$, wherein "pep*" refers to a peptide precursor of the present invention that does not interfere with the antigen binding ability of the immunoglobulin arm to which the peptide precursor is attached. In other instances, preferred V regions of an immunogen comprising a multimeric unit of the present invention include: $V_{Lpep}$-$V_H/V_L$-$V_H$; $V_{Lpep}$-$V_{Hpep}/V_L$-$V_H$; $V_L$-$V_{Hpep}/V_L$-$V_H$; $V_{Lpep}$-$V_H/V_{Lpep*}$-$V_H$; $V_{Lpep}$-$V_H/V_L$-$V_{Hpep*}$; $V_{Lpep}$-$V_H/V_{Lpep*}$-$V_{Hpep*}$; $V_L$-$V_{Hpep}/V_{Lpep*}$-$V_H$; $V_L$-$V_{Hpep}/V_L$-$V_{Hpep*}$; $V_L$-$V_{Hpep}/V_{Lpep*}$-$V_{Hpep*}$; $V_{Lpep}$-$V_{Hpep}/V_{Lpep*}$-$V_H$; $V_{Lpep}$-$V_{Hpep}/V_L$-$V_{Hpep*}$; or $V_{Lpep}$-$V_{Hpep}/V_{Lpep*}$-$V_{Hpep*}$, wherein "pep*" refers to a peptide precursor of the present invention that does not interfere with the antigen binding ability of the immunoglobulin arm to which the peptide precursor is attached.

A preferred immunogen of the present invention comprises an immunoglobulin fusion protein having a γ, α or μ C region, with an immunogen having a μ C region being more preferred.

An immunogen of the present invention is capable of inducing production of at least about 25 units of IL-2, preferably at least about 30 units of IL-2, and more preferably at least about 35 units of IL-2 by a T cell hybridoma (according to the method described in detail in Example 1).

A toleragen of the present invention is capable of inducing immunological unresponsiveness to an antigen by delivering a peptide precursor to an APC in such a manner that the APC is not capable of activating a T cell. In addition, a toleragen can be capable of delivering a peptide precursor to an APC in such a manner that the APC is capable of anergizing or killing a T cell. A preferred immunogen of the present invention comprises a monovalent (as defined above) immunoglobulin fusion protein capable of binding to only one antigen on the surface of an APC. As such, a suitable toleragen comprises two arms, wherein one arm is incapable of binding to an antigen on the surface of an APC. Preferred V regions of a toleragen of the present invention include $V_{Lpep}$-$V_H/V_L$-$V_H$; $V_L$-$V_{Hpep}/V_L$-$V_H$; $V_{Lpep}$-$V_{Hpep}/V_L$-$V_H$; $V_{Lpep}$-$V_H/V_{Lpep*}$-$V_H$; $V_{Lpep}$-$V_H/V_L$-$V_{Hpep*}$; $V_{Lpep}$-$V_H/V_{Lpep*}$-$V_{Hpep*}$; $V_L$-$V_{Hpep}/V_{Lpep*}$-$V_H$; $V_L$-$V_{Hpep}/V_L$-$V_{Hpep*}$; $V_L$-$V_{Hpep}/V_{Lpep*}$-$V_{Hpep*}$; or $V_{Lpep}$-$V_{Hpep}/V_{Lpep*}$-$V_{Hpep*}$, wherein "pep*" refers to a peptide precursor of the present invention that does not interfere with the antigen binding ability of the immunoglobulin arm to which the peptide precursor is attached.

A therapeutic reagent includes an immunoglobulin fusion protein associated with a suitable carrier. An immunoglobulin fusion protein of the present invention can also be used to produce an experimental reagent. An experimental reagent is a reagent useful for the study of different aspects of an immune response. An experimental reagent includes an immunoglobulin fusion protein associated with a suitable carrier.

As used herein, a "carrier" refers to any substance suitable as a vehicle for delivering an immunoglobulin fusion protein to a suitable in vitro or in vivo site of action. As such, carriers can act as an excipient for formulation of a therapeutic or experimental reagent containing an immunoglobulin fusion protein. Preferred carriers are capable of maintaining an immunoglobulin fusion protein in a form that is capable of binding to an antigen on the surface of an APC. Examples of such carriers include, but are not limited to water, phosphate buffered saline, saline, Ringer's solution, dextrose solution, serum-containing solutions, Hank's solution and other aqueous physiologically balanced solutions. Aqueous carriers can also contain suitable auxiliary substances required to approximate the physiological conditions of the recipient, for example, enhancement of chemical stability and isotonicity. Suitable auxiliary substances include, for example, sodium acetate, sodium chloride, sodium lactate, potassium chloride, calcium chloride, sorbitan monolaurate, triethanolamine oleate, and other substances used to produce phosphate buffer, Tris buffer, and bicarbonate buffer. Auxiliary substances can also include preservatives, such as thimerosal, m or o-cresol, formalin and benzyl alcohol. Preferred auxiliary substances for aerosol delivery include surfactant substances nontoxic to a recipient, for example, esters or partial esters of fatty acids containing from about 6 to about 22 carbon atoms. Examples of esters include, caproic, octanoic, lauric, palmitic, stearic, linoleic, linolenic, olesteric, and oleic acids. Reagents of the present invention can be sterilized by conventional methods and/or lyophilized. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

A therapeutic reagent can further comprise an immunoglobulin fusion protein combined with a compound capable of regulating an immune response. Such regulatory compounds include, but are not limited to, human gamma globulin, lymphokines, alum and/or superantigens.

In certain circumstances, carriers of the present invention can also include adjuvants including, but not limited to, Freund's adjuvant; immunostimulatory complexes (ISCOMs); other bacterial cell wall components; aluminum-based salts; calcium-based salts; silica; polynucleotides; toxoids; serum proteins; viral coat proteins; and other bacterial-derived preparations.

Useful carriers for membrane-bound immunoglobulin fusion proteins include any artificial or natural lipid-containing substrate, preferably cells, cellular membranes, liposomes and micelles. Cellular carriers of the present invention include cells capable of producing an immunoglobulin molecule. Preferred mammalian cells of the present invention include myeloma or hybridoma cells.

One aspect of the present invention is a method to regulate an immune response by administering to an animal an effective amount of an immunoglobulin fusion protein of the present invention as disclosed herein. Acceptable protocols to administer therapeutic reagents in an effective manner include individual dose size, number of doses, frequency of dose administration, and mode of administration. Determination of such protocols can be accomplished by those skilled in the art depending upon a variety of variables, including the animal to be treated and the stage of disease.

Effective doses to tolerize an animal include doses administered over time that are capable of alleviating an immune response by the animal. For example, a first tolerizing dose can comprise an amount of a toleragenic therapeutic reagent of the present invention that causes a minimal immune response when administered to an animal. A second tolerizing dose can comprise a greater amount of the same toleragenic therapeutic reagent than the first dose. Effective tolerizing doses can comprise increasing concentrations of the toleragenic therapeutic reagent necessary to tolerize an animal such that the animal does not have an immune response to subsequent exposure to the antigen contained in the toleragenic therapeutic reagent. A suitable single dose of a toleragenic immunoglobulin fusion protein of the present invention is a dose that is capable of substantially inhibiting a T cell response to an antigen when administered one or more times over a suitable time period. A preferred single dose of a toleragenic immunoglobulin fusion protein ranges from about 0.01 µg to about 1,000 milligrams (mg) of a toleragenic therapeutic reagent per subject, more preferred ranges being from about 0.1 µg to about 100 mg of a toleragenic therapeutic reagent per subject, and even more preferred ranges being from about 1 µg to about 10 mg of a toleragenic therapeutic reagent per subject.

Effective doses to immunize an animal include doses administered over time that are capable of increasing immunoglobulin molecule production to an antigen by the animal. For example, a subject first immunizing dose can comprise an amount of a immunogenic therapeutic reagent of the present invention that causes a primary immune response when administered to an animal. A second immunizing dose can comprise a lesser amount of the same therapeutic reagent than the first dose to induce a secondary immune response. For example, if a first immunization can comprise about $10^6$ arbitrary units of immunogen, then a second dose can comprise about $10^3$ arbitrary units of immunogen. Effective immunizing doses can comprise decreasing concentrations of the immunogenic therapeutic reagent necessary to maintain an animal in an immunized state, such that the animal does not have an immune response to subsequent exposure to the antigen contained in the immunogenic therapeutic reagent. A suitable single dose of a immunogenic immunoglobulin fusion protein of the present invention is a dose that is capable of substantially stimulating a T cell response to an antigen when administered one or more times over a suitable time period. A preferred single dose of a immunogenic immunoglobulin fusion protein ranges from about 0.01 µg to about 1,000 milligrams (mg) of an immunogenic therapeutic reagent per subject more preferred ranges being from about 0.1 µg to about 100 mg of a immunogenic therapeutic reagent per subject, and even more preferred ranges being from about 1 µg to about 10 mg of a immunogenic therapeutic reagent per subject.

The manner of administration of a therapeutic reagent of the present invention can depend upon the particular purpose for the delivery (e.g., treatment of disease or delivery of an imaging reagent), the overall health and condition of the recipient and the judgement of the physician or technician administering the target vehicle. A therapeutic reagent of the present invention can be administered to an animal using a variety of methods. Such delivery methods can include parenteral, topical, oral or local administration, such as intradermally or by aerosol. A therapeutic reagent can be administered in a variety of unit dosage forms depending upon the method of administration. For example, unit dosage forms suitable for oral administration to the intestinal region of an animal include powder, tablets, pills and capsules. Preferred delivery methods for a therapeutic reagent of the present invention include intravenous administration, local administration by, for example, injection, intradermal injection, intramuscular injection and inhalation. For particular modes of delivery, a therapeutic reagent of the present invention can be formulated in an excipient of the present invention. A therapeutic reagent of the present invention can be administered to any animal, preferably to mammals, and more preferably to humans.

The following experimental results are provided for purposes of illustration and are not intended to limit the scope of the invention.

EXAMPLES

Example 1

This Example demonstrates that a DNA sequence encoding OVA peptide substituted for the CDR1 domain of a kappa L chain can be expressed by a myeloma cell, internalized and processed by an APC, and presented to a T cell in such a manner that the T cell is stimulated to produce IL-2.

A. Production of the $pV_\kappa$-$OVA_{326-337}$ Construct

Figure 2:
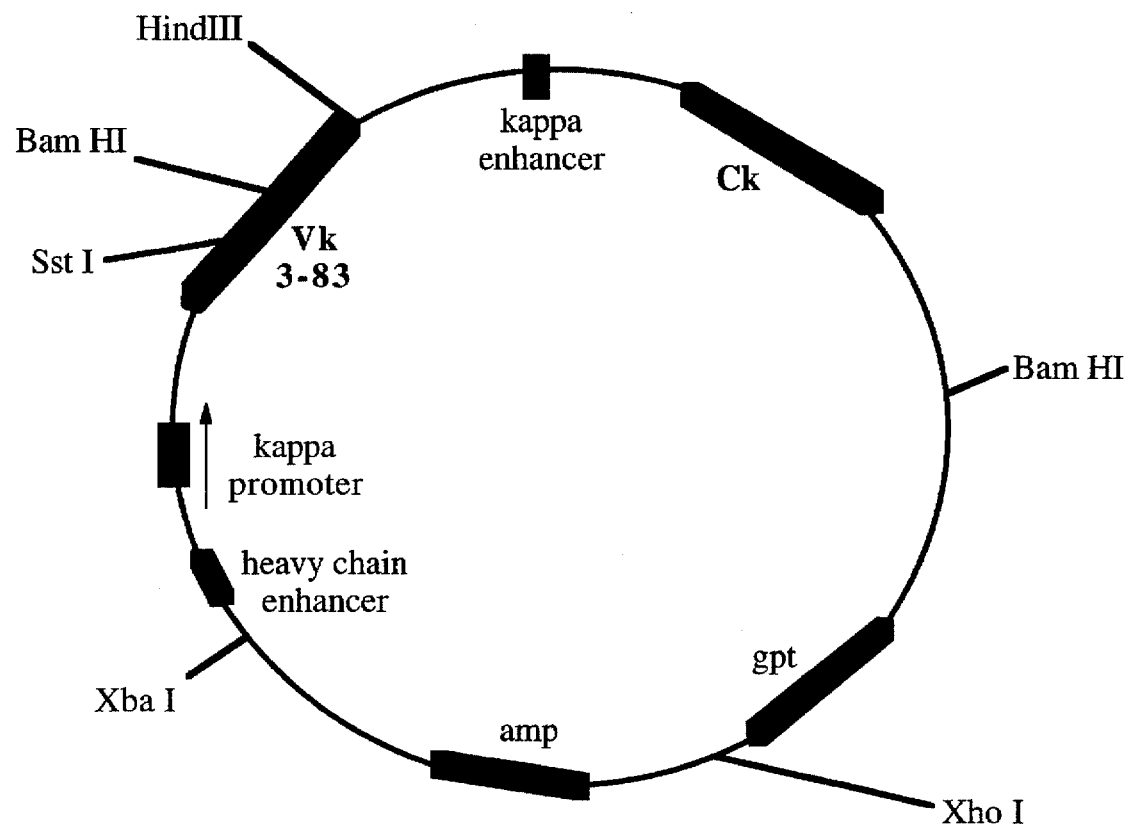

Initially, a cDNA clone encoding the mouse 3.83 kappa light chain was modified by polymerase chain reaction-based mutagenesis (described in Mullis et al, p. 253, 1986, *Cold Spring Harbor Symposium*, Vol. 51) and the V and J region was ligated into the expression vector pHT4-$Y_\kappa$-CE containing the a genomic clone of the 3.83 kappa constant region together with appropriate enhancers, promoters and selectable markers (i.e., HMX) to form the recombinant molecule p3.83 shown in FIG. 2.

The oligonucleotides used for mutagenesis were synthesized using an Applied Biosystems Nucleotide Synthesizer (Applied Biosystems, Foster City, Calif.). The mutations introduced within the CDR1 domain of the 3.83 light chain encoded amino acid residues 326 through 336 of ovalbumin protein ($OVA_{326-336}$) flanked on either side by nucleotides encoding Spe I and Bss HII restriction enzyme sites, as shown in FIG. 3. The first three nucleotides of the Bss HII restriction site also coded for the $337^{th}$ amino acid of OVA. As a result, the actual length of the OVA antigenic peptide was $OVA_{326-337}$.

Referring to FIG. 3, the oligonucleotide encoding the $OVA_{326-337}$ antigenic peptide was substituted for the portion of the p3.83 plasmid encoding the CDR1 domain of the V region of the 3.83 light chain by the method described above. The ligation product was DNA sequenced to verify the accuracy of the insertion, such as correct orientation and precise insertion. The resulting construct is referred to as $pV_\kappa$-$OVA_{326-337}$.

B. Expression of the $pV_\kappa$-$OVA_{326-337}$ Construct in SP2/0 Cells $pV_\kappa$-$OVA_{326-337}$ was purified over a cesium chloride gradient using methods standard in the art. The purified $pV_\kappa$-$OVA_{326-337}$ plasmid was then linearized by digesting the plasmid with the restriction enzyme, XhoI. Linearized $pV_\kappa$-$OVA_{326-337}$ plasmid was then transfected into SP2/0 mouse myeloma cells (which do not produce immunoglobulin) by the following electroporation method. About $1\times10^7$ SP2/0 cells were centrifuged at $\times 1,100$ rpm for 10 minutes and resuspended in phosphate buffered saline. The resuspended cells were mixed with about 10 to 20 µg of linearized $pV_\kappa$-$OVA_{326-337}$ plasmid in a volume of 0.8 ml and allowed to sit for 10 minutes on ice. The mixture was then subjected to 200 volts (960° F.)(about 800V/cm) for about 4 milliseconds. The electroporated cells were then centrifuged at $\times 1,100$ rpm and resuspended in selective medium containing hypoxanthine, xanthine and mycophenolic acid (HMX). The cells were plated in 96-well plates, with each well containing about 50,000 cells. The cells were then incubated for 10 days at 37° C. to allow for selection of cells expressing the $pV_\kappa$-$OVA_{326-337}$ plasmid. It was found that about 30% of the wells had HMX resistant clones.

Figure 4:
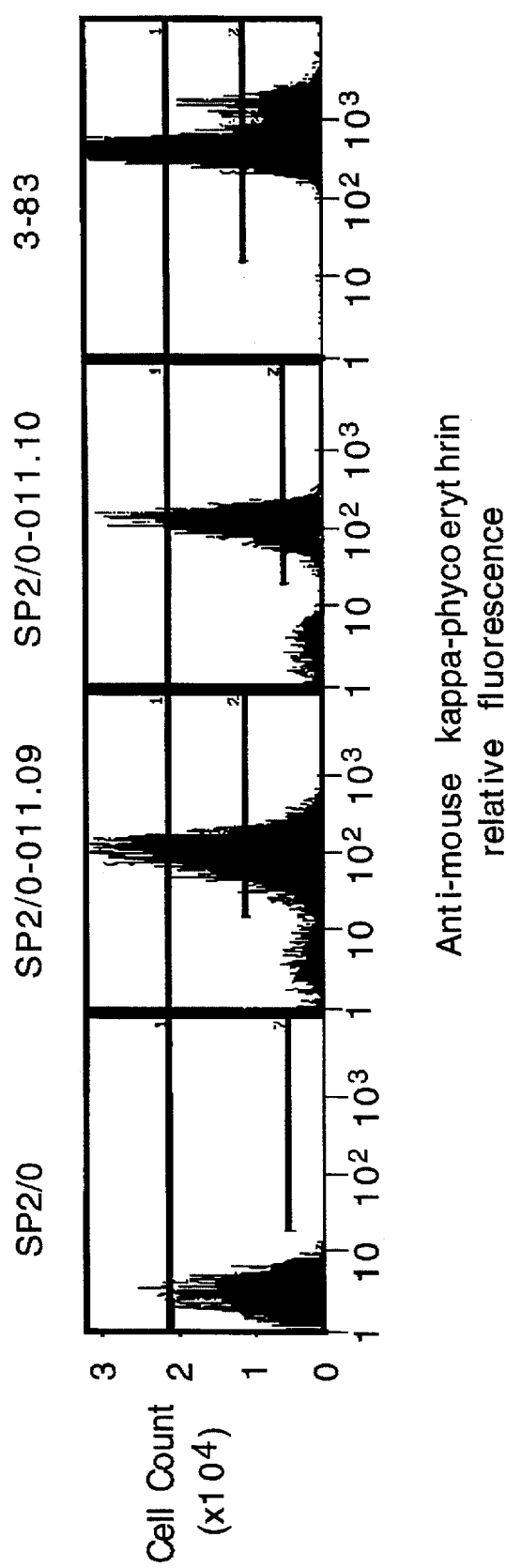

The selected cells were then screened for the presence of cytoplasmic $OVA_{326-337}$ chimeric light chain encoded by the $pV_\kappa$-$OVA_{326-337}$ plasmid by flow cytometry. About $2\times10^6$ selected cells were lightly fixed with 2% paraformaldehyde for 30 minutes at 4° C. and permeabilized with 0.2% Triton X100 for 10 minutes at 25° C. After washing, the cells were incubated with 100 µl of a 1:100 dilution of a goat anti-mouse kappa antibody conjugated with biotin (obtained from Southern Biotechnology Associates, Birmingham, Ala.) for 30 minutes at 4° C. After washing, the cells were incubated with 100 µl of streptavidinphycoerythin (obtained from Becton Dickinson, Mt. View, Calif.) for 15 minutes at 4° C., and washed again. Expression of the $OVA_{326-337}$ chimeric light chain in the SP2/0 cells was measured by passing $1\times10^4$ streptavidinphycoerythin labelled cells through a Facscan flow cytometer (Becton Dickinson, Mt. View, Calif.) The results are shown in FIG. 4 and indicate that about 80% of the drug resistant cells were found to express detectable levels of cytoplasmic kappa chain.

The drug resistant cells that were found to produce cytoplasmic $OVA_{326-337}$ chimeric light chain were screened for secreted $OVA_{326-337}$ chimeric light chain by enzyme linked immunoassay (ELISA). ELISA plates (Immulon II, Dynatech, Chantilly, Va.) were coated with 10 µg/ml rat anti-mouse kappa monoclonal antibody (187.1) and blocked with 2% bovine serum albumin in PBS for 30 minutes at 25° C. 50 µl of culture medium supernatants in which drug resistant cells had been grown were added to separate coated wells and incubated for 16 hours at 4° C. After washing, 50 µl of rat anti-mouse kappa antibody conjugated with biotin (33.18.12) (cell line provided by Dr. Fritz Melchers, Basel, Switzerland) was added to each well exposed to supernatant to detect the amount of $OVA_{326-337}$ chimeric light chain bound to the 187.1 antibody bound to the ELISA plate. It was found that about 50% of the cells positive for cytoplasmic $OVA_{326-337}$ chimeric light chain also secreted between 1–2 µg/ml of $OVA_{326-337}$ chimeric light chain. Two drug resistant cell clones which expressed high levels of cytoplasmic $OVA_{326-337}$ chimeric light chain and also secreted 2 µg/ml of $OVA_{326-337}$ chimeric light chain were selected for further experiments.

C. Processing and Presentation of $OVA_{326}$-337 chimeric light chain

The secreted $OVA_{326-337}$ chimeric light chain present in the supernatants of SP2/0 transfectomas were tested for their ability to be processed and presented by an antigen presenting cell (APC) in such a manner that the presented antigen could stimulate OVA peptide specific T cells. Two T cell hybridomas that express T cell receptors (TCR) capable of binding to MHC class II complexed with OVA peptides and secrete IL-2 upon stimulation were chosen. The TCR on hybridoma 3D0.54.8 can bind to MHC class II molecules complexed with $OVA_{326-336}$ peptides. The TCR on hybridoma, D0.11.10/54.4 can bind to MHC class II molecules complexed with $OVA_{323-336}$ peptides for optimal stimulation and $OVA_{326-336}$ for poor stimulation.

Supernatants were recovered from the two drug resistant SP2/0 transfectomas and pooled. The pooled supernatants were concentrated 30× using 50% ammonium sulfate precipitation. In addition, control samples were prepared by concentrating in parallel, the supernatants from non-transfected SP2/0 cells. Twelve μl or 110 μl of the 30× concentrated supernatants or ovalbumin (1 mg/ml) were mixed with $1\times10^5$ A20.G3 APCs ($IA^d$ expressing B cell lymphoma) and either $1\times10^5$ 3DO.54.8 or DO.11.10/54.4 T cell hybridoma cells. After culturing for 24 hours, the stimulation of the T cell hybridomas was assessed by measuring the levels of IL-2 in the culture supernatants by performing a biological assay using IL-2 dependent, HT-2 cells (described in Kappler et al., p. 153, 1981, *J. Exp. Med.*, Vol. 153 and Masmann, pp. 55–63, 1983, *J. Immunol. Met.*, Vol. 65).

Figure 5:
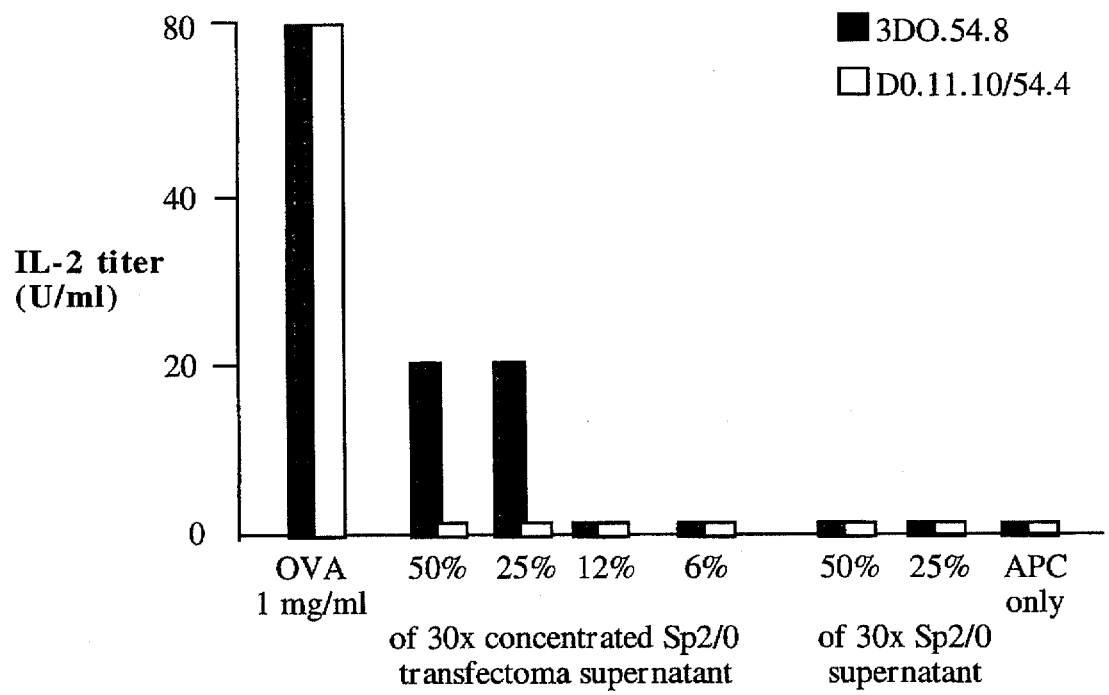

Referring to FIG. 5, the results indicate that the T cell hybridoma, 3DO.54.8 but not DO.11.10/54.4 was significantly stimulated to secrete IL-2 by the SP2/0 transfectoma supernatants at the 25% and 50% concentrations. Thus indicating that the $OVA_{326-336}$ peptide was properly processed from the $OVA_{326-337}$ chimeric light chain and presented by the APC cell to the 3DO.54.8 $OVA_{326-336}$ specific T cell. The control SP2/0 supernatants or the APC alone samples failed to induce either of the T cell hybridomas to produce IL-2, whereas ovalbumin stimulated both T cell hybridomas. The difference in IL-2 stimulation between the OVA and the $OVA_{326-337}$ chimeric light chain at the 25% and 50% concentrations is due to differences in concentration. The 30× concentrated supernatant contained a maximum of 60 μg/ml of $OVA_{326-337}$ chimeric light chain compared to 1 mg/ml of ovalbumin. Thus, the lower levels of IL-2 stimulation by APCs treated with $OVA_{326-337}$ chimeric light chain and APCs treated with OVA is likely to be due to concentration differences.

Example 2

This Example demonstrates the expression of a DNA encoding an OVA peptide substituted for the CDR1 domain of a kappa L chain in a hybridoma cell expressing a compatible H chain, the internalization and processing of the immunoglobulin fusion protein by an APC, and the presentation of the OVA antigenic peptide to a T cell in such a manner that the T cell is stimulated to produce IL-2.

A. Production of an $OVA_{326-337}$-Containing Immunoglobulin Fusion Protein

The purified and linearized $pV_\kappa$-$OVA_{326-337}$ plasmid (described in detail in Example 1) and $pV_\kappa$-OVA (encoding the V and C region of the mouse 3.83 kappa light chain, without $OVA_{326-337}$ peptide substituted in for the CDR1 domain) are electroporated into the 33D1 B cell hybridoma expressing the wildtype 33D1 H and L chains. The plasmids are electroporated into the 33D1 B cell hybridoma using the method described in Example 1. Drug resistant cell clones are established as described above in Example 1.

Production of $OVA_{326-337}$ chimeric light chain by drug resistant 33D1 B cell hybridomas are screened by ELISA and flow cytometry using the methods described in Example 1. Antibodies contained in culture medium supernatants from 33D1 B cell hybridomas producing $OVA_{326-337}$ chimeric light chain are isolated by passing the supernatants over a protein A or protein G sepharose column. Bound immunoglobulin molecules are eluted using glycine HCl, pH 3.5, neutralized and dialyzed against phosphate buffered saline. The presence of antibodies having activity in the eluant is assessed by flow cytometry using fluorescein-labelled rat anti-mouse kappa monoclonal antibodies.

Antibodies having $OVA_{326-337}$ chimeric light chain and antibodies having wildtype light chain are separated by chromatographic techniques. Chromatography fractions from the separation experiments are tested for the presence of an immunoglobulin fusion protein using one or both of the following assays. The first assay tests the specific binding of antibodies to APCs using flow cytometry. Chromatography fractions containing antibodies are incubated with APCs and then the APCs are isolated by centrifugation. The isolated APCs are then incubated with a labelled antibody capable of binding to the antibody from the chromatography fractions (for example, the fluorescein-labelled rat anti-mouse kappa monoclonal antibodies described above). After washing, the presence of fluorescent APCs indicates the presence of antibody bound to the surface of the APC. The second assay is a biological assay which tests for the presence of $OVA_{326-337}$ chimeric light Chain in antibodies bound to APCs. The test measures the ability of an antibody to stimulate OVA peptide specific T cell hybridomas in the presence of APC the method described in Example 1. The combined results of the first and second test indicate the presence of immunoglobulin fusion proteins having $OVA_{326-337}$ chimeric light chains in the chromatographic fractions.

B. APC-Specific Targeting

The specific APC antigen binding by immunoglobulin fusion proteins is tested by two methods. The first method involves incubating APCs with an Fc receptor specific antibody prior to incubation with the immunoglobulin fusion protein. Binding of an immunoglobulin fusion protein to the APC is measured as described above. The presence of binding of the immunoglobulin fusion protein to the APCs indicates antigen specific, non-Fc receptor, binding. The second method involves binding immunoglobulin fusion proteins comprising F(ab')$_2$ fragments to APCs to avoid Fc receptor binding via the C region of the immunoglobulin fusion protein. The presence of F(ab')$_2$ fragment binding to the APCs is measured using an antibody that binds to the V region or the light chain C region of the F(ab')$_2$ fragment (for example, the fluorescein-labelled rat anti-mouse kappa monoclonal antibodies described above). The binding of F(ab')$_2$ fragment to the APCs indicates antigen specific, non-Fc receptor, binding.

C. Presentation of Antigenic Peptide by an APC to a T Cell

The $OVA_{326-337}$ chimeric immunoglobulin fusion proteins are tested for their ability to be processed and presented by an antigen presenting cell (APC) in such a manner that the presented antigen stimulates OVA peptide specific T cells using the methods described in Example 1 with substitutions of the fusion proteins for the chimeric light chain. IL-2 production by T cells incubated with APCs treated with the $OVA_{326-337}$ chimeric immunoglobulin fusion protein indicates that the $OVA_{326-337}$ peptide is processed and presented in such a manner that the peptide is capable of stimulating the T cell.

Example 3

This example describes the production of chimeric light chains containing antigenic peptides involved in the autoimmune disease murine myasthenia gravis.

Oligonucleotides are synthesized that encode for antigenic peptides derived from the Acetyl Choline Receptor (AChR) of the electric fish (*Torpedo californica*). Such oligonucleotides are termed $AChR_{146-162}$ which encodes for amino acid residues 146 through 162 of the acetyl choline receptor and $AChR_{111-126}$ which encodes for amino acid residues 111 through 126 of the acetyl choline receptor. The oligonucleotides are also flanked by DNA sequence allowing ligation into the CDR1 domain of a light chain which is excised out using appropriate restriction enzymes. Such ligation products are referred to as pVK-AChR$_{146-162}$ and pV$_\kappa$-AChR$_{111-126}$.

Purified and linearized pV$_\kappa$-AChR$_{146-162}$ or pV$_\kappa$-AChR$_{111-126}$ plasmid are then transfected into a B cell hybridoma expressing a compatible H and L chain, and drug resistant cell clones expressing AChR$_{146-162}$ or AChR$_{111-126}$ chimeric light chains are identified using the methods disclosed in Example 1. Drug resistant cell clones secreting immunoglobulin fusion proteins having the compatible H chain combined with the AChR$_{146-162}$ or AChR$_{111-126}$ chimeric light chains are identified using the methods described in Example 2.

The specific targeting of the immunoglobulin fusion proteins having the AChR$_{146-162}$ or AChR$_{111-126}$ chimeric light chains to an APC is determined using the methods described in Example 2. The ability of the AChR$_{146-162}$ peptide or the AChR$_{111-126}$ peptide to be processed and presented by the APC to a T cell in such a manner that the T cell is activated to secrete IL-2 is determined using the methods described in Example 1. Stimulation of IL-2 production by APCs treated with the immunoglobulin fusion protein having the AChR$_{146-162}$ or AChR$_{111-126}$ chimeric light chains indicates that following specific immunotargeting, the peptide is properly processed and presented by the target APCs.

Example 4

This example describes an experiment to assess the size constraints of substituting an antigenic peptide for the CDR1 domain of a L chain such that the immunotargeting and presentation function of an immunoglobulin fusion protein are not impaired.

An oligonucleotide is synthesized that encodes for an antigenic peptide derived from ovalbumin (OVA). The oligonucleotide encodes for amino acid residues 323 through 340 of ovalbumin protein ($OVA_{326-336}$) flanked on either side by nucleotides encoding Spe I and Bss HII restriction enzyme sites. The oligonucleotide encoding the $OVA_{323-340}$ antigenic peptide is substituted for the portion of the p3.83 plasmid encoding the CDR1 domain of the V region of the 3.83 light chain using the methods described in Example 1 to form the recombinant molecule $pV_\kappa$-$OVA_{323-340}$.

Purified and linearized $pV_\kappa$-$OVA_{323-340}$ plasmid is then transfected into the 33D1 B cell hybridoma expressing the 33D1 H and L chains and drug resistant cell clones expressing $OVA_{323-340}$ chimeric light chain are identified using the methods disclosed in Example 1. Drug resistant cell clones secreting immunoglobulin fusion protein having the 33D1 H chain combined with the $OVA_{323-340}$ chimeric light chain are identified using the methods described in Example 2. Specific binding of the immunoglobulin fusion protein having the $OVA_{323-340}$ chimeric light chain indicates that the 17 amino acid long peptide does not impair the immunotargeting function of the immunoglobulin fusion protein.

The specific targeting of the immunoglobulin fusion protein having the $OVA_{323-340}$ chimeric light chain to an APC is determined using the methods described in Example 2. The ability of the $OVA_{323-340}$ peptide to be processed and presented by the APC to a T cell in such a manner that the T cell is activated to secrete IL-2 is determined using the methods described in Example 1. Stimulation of IL-2 production by APCs treated with the immunoglobulin fusion protein having the $OVA_{323-340}$ chimeric light chain indicates that following specific immunotargeting, the peptide is properly processed and presented by the target APCs.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed:

1. An immunoglobulin fusion protein which delivers a peptide comprising an antigenic peptide to a targeted antigen presenting cell, comprising an immunoglobulin molecule linked within the variable region of said immunoglobulin molecule to a peptide comprising an antigenic peptide, wherein said variable region binds to a target antigen on the surface of a specific antigen presenting cell thereby targeting said immunoglobulin fusion protein to said specific antigen presenting cell.

2. The immunoglobulin fusion protein of claim 1, wherein said immunoglobulin molecule is from an animal selected from the group consisting of human, mouse, rat and hamster.

3. The immunoglobulin fusion protein of claim 1, wherein said immunoglobulin molecule is from a human.

4. The immunoglobulin fusion protein of claim 1, wherein said immunoglobulin fusion protein is secreted from a cell that produces said protein.

5. The immunoglobulin fusion protein of claim 1, wherein said variable region binds to a target antigen on the surface of an antigen presenting cell selected from the group consisting of a dendritic cell, a macrophage and B lymphocyte.

6. The immunoglobulin fusion protein of claim 1, wherein said variable region binds to a target antigen on the surface of a non-professional antigen presenting cell.

7. The immunoglobulin fusion protein of claim 1, wherein said variable region binds to a target antigen on the surface of a professional antigen presenting cell.

8. The immunoglobulin fusion protein of claim 1, wherein said variable region binds to a target antigen on the surface of an antigen presenting cell which activates a $T_H2$ cell.

9. The immunoglobulin fusion protein of claim 1, wherein said variable region binds to a target antigen selected from the group consisting of a class I molecule, a class II molecule, membrane-bound IgM, membrane-bound IgD, membrane-bound IgA, B7, B7-2, CD10, CD11c, CD13, CD19, CD22, CD33, CD35, CD38, CD40, CD45, CD45R, MAC-1, LFA-3, ICAM-1, ICAM-2, ICAM-3, VLA-4, CD22, 33D1, R4/23, F4/80, and KiM4.

10. The immunoglobulin fusion protein of claim 1, wherein said variable region binds to a target antigen selected from the group consisting of a membrane-bound IgM, membrane-bound IgD, membrane-bound IgA, B7, B7-2, CD10, CD19, CD22, CD38, CD40, and CD45R.

11. The immunoglobulin fusion protein of claim 1, wherein said variable region binds to a target antigen selected from the group consisting of a B7 molecule and a B7–2 molecule.

12. The immunoglobulin fusion protein of claim 1, wherein said variable region binds to a membrane-bound IgM, membrane-bound IgD, membrane-bound IgA, CD45R, CD22, CD13, CD33, F4/80, 33D1, R4/23, KiM4, CD35, B7-2, CD11c, and MHC class II.

13. The immunoglobulin fusion protein of claim 1, wherein said immunoglobulin molecule further comprises a constant region.

14. The immunoglobulin fusion protein of claim 13, wherein said constant region is selected from the group consisting of human κ, λ, μ, γ1, γ2, γ3, γ4, α1, α2, δ and ε constant regions.

15. The immunoglobulin fusion protein of claim 1, wherein said peptide comprising an antigen peptide binds to the peptide binding site of an MHC molecule.

16. The immunoglobulin fusion protein of claim 1, wherein said antigenic peptide is a class II restricted peptide.

17. The immunoglobulin fusion protein of claim 1, wherein said peptide comprising an antigenic peptide comprises from about 5 to about 40 amino acid residues.

18. The immunoglobulin fusion protein of claim 1, wherein said peptide comprising an antigenic peptide comprises from about 9 to about 30 amino acid residues.

19. The immunoglobulin fusion protein of claim 1, wherein said peptide comprising an antigenic peptide comprises from about 12 to about 18 amino acid residues.

20. The immunoglobulin fusion protein of claim 1 which comprises two or more peptides comprising antigenic peptides.

21. The immunoglobulin fusion of claim 1, wherein said peptide comprising an antigenic peptide is linked to said variable region by a recombinantly produced peptide bond.

22. The immunoglobulin fusion protein of claim 1, wherein said peptide comprising an antigenic peptide is substituted within a complementarity-determining region in a $V_L$ region of said immunoglobulin molecule.

23. The immunoglobulin fusion protein of claim 22, wherein said complementarity-determining region comprises a CDR1 domain of said $V_L$ region.

24. The immunoglobulin fusion protein of claim 1 which is monovalent.

25. The immunoglobulin fusion protein of claim 1 which is multivalent. immunoglobulin fusion protein is monovalent.

26. An immunoglobulin fusion protein which delivers a peptide comprising an antigenic peptide to a targeted antigen presenting cell, comprising an immunoglobulin molecule linked within the variable region of said immunoglobulin molecule with a peptide comprising an antigenic peptide, wherein said variable region binds to a target antigen on said targeted antigen presenting cell that distinguishes between types of antigen presenting cells.

27. The immunoglobulin fusion protein of claim 26, wherein said target antigen is selected from the group consisting of a membrane-bound IgM, membrane-bound IgD, membrane-bound IgA, CD45R, CD22, CD13, CD33, F4/80, 33D1, R4/23, KiM4, CD35, B7-2, CD11c, and MHC class II.

\* \* \* \* \*

UNITED STATES PATENT AND TRADEMARK OFFICE
CERTIFICATE OF CORRECTION

PATENT NO. : 5,698,679
DATED : December 16, 1997
INVENTOR(S) : Nemazee

It is certified that error appears in the above-identified patent and that said Letters Patent is hereby corrected as shown below:

In Claim 15, line 66, please delete "antigen" and insert therefor --antigenic--.
In Claim 23, line 22, please delete "Theimmunoglobulin" and insert therefor --The immunoglobulin--.
In Claim 25, lines 4-5, following "multivalent.", please delete --immunoglobulin fusion protein is monovalent.--.

Signed and Sealed this

Twenty-first Day of April, 1998

Attest:

BRUCE LEHMAN

*Attesting Officer*  *Commissioner of Patents and Trademarks*